(12) United States Patent
Van Bruggen et al.

(10) Patent No.: US 7,998,931 B2
(45) Date of Patent: Aug. 16, 2011

(54) VASCULAR ENDOTHELIAL CELL GROWTH FACTOR ANTAGONISTS AND USES THEREOF

(75) Inventors: Nicholas Van Bruggen, San Carlos, CA (US); Napoleone Ferrara, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 137 days.

(21) Appl. No.: 12/107,041

(22) Filed: Apr. 21, 2008

(65) Prior Publication Data

US 2008/0299116 A1 Dec. 4, 2008

Related U.S. Application Data

(63) Continuation of application No. 10/683,043, filed on Oct. 9, 2003, now abandoned, which is a continuation of application No. 09/218,481, filed on Dec. 22, 1998, now abandoned.

(51) Int. Cl.
*A61K 38/17* (2006.01)
*A61K 39/395* (2006.01)
*C07K 16/46* (2006.01)
*C07K 14/71* (2006.01)

(52) U.S. Cl. ........ 514/12; 514/2; 424/134.1; 424/192.1; 530/373.3; 530/402

(58) Field of Classification Search ............... 530/373.3, 530/402; 424/134.1, 192.1; 514/2, 12, 7.5, 514/13.3, 21.3, 21.2, 870
See application file for complete search history.

(56) References Cited

U.S. PATENT DOCUMENTS

| | | | |
|---|---|---|---|
| 4,456,550 A | 6/1984 | Dvorak et al. |
| 5,036,003 A | 7/1991 | Olander et al. |
| 5,306,710 A | 4/1994 | Wei |
| 5,518,999 A | 5/1996 | Nakamura et al. |
| 5,955,311 A | 9/1999 | Rockwell et al. |
| 6,093,740 A | 7/2000 | Jirousek et al. |
| 6,114,320 A | 9/2000 | Aiello et al. |
| 6,177,401 B1 | 1/2001 | Ullrich et al. |
| 6,884,879 B1 | 4/2005 | Baca et al. |
| 7,060,269 B1 | 6/2006 | Baca et al. |
| 2005/0053599 A1 | 3/2005 | Van Bruggen et al. |
| 2005/0244405 A1 | 11/2005 | Van Bruggen et al. |
| 2007/0110755 A1 | 5/2007 | Ferrara et al. |
| 2008/0181900 A1 | 7/2008 | Ferrara et al. |
| 2008/0187534 A1 | 8/2008 | Baca et al. |
| 2008/0226629 A1 | 9/2008 | Baca et al. |
| 2008/0299116 A1 | 12/2008 | Van Bruggen et al. |
| 2008/0311118 A1 | 12/2008 | Van Bruggen et al. |
| 2009/0081232 A1 | 3/2009 | Kim et al. |

FOREIGN PATENT DOCUMENTS

| | | |
|---|---|---|
| CA | 2355976 | 12/1999 |
| EP | 1238986 | 9/2002 |
| EP | 1140173 B1 | 8/2005 |
| JP | 04506659 | 11/1992 |
| JP | 08502514 | 3/1996 |
| WO | WO 92/14748 | 9/1992 |
| WO | 94/10202 | 5/1994 |
| WO | WO 96/30046 | 10/1996 |
| WO | WO 97/40831 | 11/1997 |
| WO | WO 97/44453 | 11/1997 |
| WO | WO 97/49408 | 12/1997 |
| WO | 98/16551 | 4/1998 |
| WO | WO 98/45331 | 10/1998 |
| WO | WO 98/48795 | 11/1998 |
| WO | WO 98/52577 | 11/1998 |
| WO | WO 00/27414 | 5/2000 |
| WO | WO 00/29584 | 5/2000 |
| WO | WO 00/37502 | 6/2000 |

OTHER PUBLICATIONS

Severinghaus, J.W., et al. J. Appl. Physiol., 79(2): 375-379, 1995.*
Heiss, J. D., et al., Journal of Clinical Investigation, 98(6): 1400-1408, 1996.*
Aiello, L.P., et al. Proc. Natl. Acad. Sci., 92: 10457-10461, 1995.*
Jin, D.P., et al. Lymphatic Research and Biology, 7(1): 47-57, 2009.*
Kajiya, K. et al., Journal of Investigative Dermatology, 129: 1292-1298, 2009.*
Nag, S., et al. Journal of Neuropathology and Experimental Neurology, 56(8): 912-921, 1997.*
Berkman et al., "Expression of the vascular permeability factor/vascular endothelial growth factor gene in central nervous system neoplasms" *J. Clin. Invest.* 91:153-159 (Jan. 1993).
Risau, W., "Molecular biology of blood-brain barrier ontogenesis and function" *Acta Neurochirurgica* (abstract only) 60:109-112 (1994).
*Taber's Cyclopedic Medical Dictionary*, 16th edition, Philadelphia:F.A. Davis Company pp. 742 (1989).
van Bruggen et al., "VEGF antagonism reduces edema formation and tissue damage after ischemia/reperfusion injury in the mouse brain" *Journal of Clinical Investigation* 104(11):1613-1620 (Dec. 1999).
U.S. Appl. No. 09/218,418, Dec. 22, 1998, Van Bruggen et al.
U.S. Appl. No. 09/718,694, Nov. 21, 2000, Van Bruggen et al.
Genentech, Inc., 2009, AVASTIN™ (Bevacizumab) Labeling Text, U.S. BL 125085/169 Amendment.
Adamis et al., 1996, "Inhibition of Vascular Endothelial Growth Factor Prevents Retinal Ischemia-Associated Iris Neovascularization in a Nonhuman Primate," Arch. Ophthalmol., 114:66-71.
Aiello et al., 1994, "Vascular endothelial growth factor in ocular fluid of patients with diabetic retinopathy and other retinal disorders," The New England Journal of Medicine, 331(22):1480-1486.
Aiello et al., 1996, "Vascular endothelial growth factor (VEGF) increases retinal vascular permeability in vivo," Investigative Ophthalmology & Visual Science, 37(3), Abstract 578-B490.
Aiello et al., 1997, "Vascular Endothelial Growth Factor-Induced Retinal Permeability Is Mediated by Protein Kinase C In Vivo and Suppressed by an Orally Effective β-Isoform-Selective Inhibitor," Diabetes, 46:1473-1480.
Ambati et al., 1997, "Elevated γ-Aminobutyric Acid, Glutamate, and Vascular Endothelial Growth Factor Levels in the Vitreous of Patients With Proliferative Diabetic Retinopathy," Arch. Ophthalmol., 115:1161-1166.
Arimura et al., 1997, "Two cases of POEMS syndrome with increased vascular endothelial growth factor (VEGF)," Clin. Neurol., 37(9):817-823 (in Japanese with English abstract).
Arimura et al., 1998, "Characteristic edema in Crow-Fukase syndrome," Neurol. Med., 49:248-249 (in Japanese).

(Continued)

*Primary Examiner* — Alana M. Harris
*Assistant Examiner* — Anne L Holleran
(74) *Attorney, Agent, or Firm* — Jones Day

(57) ABSTRACT

The present invention provides vascular endothelial cell growth factor (VEGF) antagonists and methods of using VEGF antagonists. VEGF antagonists contemplated by the invention include VEGF antibodies and VEGF receptor fusion proteins. Methods of treating edema and stroke using VEGF antagonists are also provided.

10 Claims, 13 Drawing Sheets

OTHER PUBLICATIONS

Arimura et al., 1998, "The pathophysiology of Crow-Fukase syndrome," Neuroimm., 6(2)1-6 (in Japanese with English abstract).
Asano et al., 1998, "An anti-human VEGF monoclonal antibody, MV833, that exhibits potent anti-tumor activity in vivo," Hybridoma, 17(2):185-190.
Bae et al., 2000, "Arginine-rich anti-vascular endothelial growth factor peptides inhibit tumor growth and metastasis by blocking angiogenesis," The Journal of Biological Chemistry, 275(18):13588-13596.
Bae et al,, 2005, "Anti-flt1 peptide, a vascular endothelial growth factor receptor 1-specific hexapeptide, inhibits tumor growth and metastasis," Clin Cancer res., 11(7):2651-2661.
Baker et al., 1995, "Elevated Serum Levels of Vascular Endothelial Growth Factor in Patients With Preeclampsia," Obstetrics & Gynecology, 86(5):815-821.
Barleon et al., "Differential Expression of the Two VEGF Receptors flt and KDR in Placenta and Vascular Endothelial Cells," J. Cell Biochem., 1994,54(1):56-66.
Bates, D.O. et al., 1996. "Vascular endothelial growth factor increases hydraulic conductivity of isolated perfused microvessels," Am. J. Physiol. 271: H2520-H2528.
Batzdorf, 1976, "The management of cerebral edema in pediatric practice," Pediatrics, 58:78-87.
Bennett et al., 1991, "Extracellular Domain-IgG Fusion Proteins for Three Human Natriuretic Peptide Receptors. Hormone Pharmacology and Application to Solid Phase Screening of Synthetic Peptide Antisera," J. Biol. Chem., 266(34):23060-23067.
Brauchle et al., 1996, "Ultraviolet Band H2O 2 Are Potent Inducers of Vascular Endothelial Growth Factor Expression in Cultured Keratinocytes," J. Biol. Chem., 271(36):21793-21797.
Brekken et al., 1998, "Vascular endothelial growth factor as a marker of tumor endothelium," Cancer Research, 58:1952-1959.
Brekken et al., 2000, "Selective inhibition of vascular endothelial growth factor (VEGF) receptor 2 (KDR/Flk-1) activity by a monoclonal anti-VEGF antibody blocks tumor growth in mice," Cancer Research, 60:5117-5124.
Burgess et al., 1989, "The Heparin-Binding (Fibroblast) Growth Factor Family of Proteins," Annu. Rev. Biochem., 58:575-606.
Chen et al., 1986, "A Model of Focal Ischemic Stroke in the Rat: Reproducible Extensive Cortical Infarction," Stroke, 17(4):738-743.
Cheng et al., 1997, "Intracerebral tumor-associated hemorrhage caused by overexpression of the vascular endothelial growth factor isoforms $VEGF_{121}$ and $VEGF_{165}$ but not $VEGF_{189}$," Proc. Natl. Acad. Sci. USA, 94:12081-12087.
Chisholm et al., 1995, "DNA Cloning 4: A Practical Approach," Mammalian Systems, pp. 1-39.
Collins et al., 1993, "Characterization of the Increase in Vascular Permeability Induced by Vascular Permeability Factor in vivo," Br. J. Pharmacol., 109:195-199.
Connolly et al., 1989, "Human Vascular Permeability Factor. Isolation from U937 Cells," J Biol. Chem., 264(33):20017-20024.
Connolly et al., 1989, "Tumor Vascular Permeability Factor Stimulates Endothelial Cell Growth and Angiogenesis," J. Clin. Invest., 84(5):1470-1478.
Criscuolo, 1993, "Clinical Neurosciences in the Decade of the Brain Hypotheses in Neuro-Oncology: The Genesis of Peritumoral Vasogenic Brain Edema and Tumor Cysts: A Hypothetical Role for Tumor-Derived Vascular Permeability Factor," Yale Journal of Biology and Medicine, 66:277-314.
Davis-Smyth et al., 1996, "The Second Immunoglobulin-like Domain of the VEGF Tyrosine Kinase Receptor Flt-1 Determines Ligand Binding and may Initiate a Signal Transduction Cascade," EMBO J., 15(18):4919-4927.
De Vries et al., 1992, "The fms-like Tyrosine Kinase, a Receptor for Vascular Endothelial Growth Factor," Science, 255(5047):989-991.
Detmar et al., 1997, "Hypoxia Regulates the Expression of Vascular Permeability Factor/Vascular Endothelial Growth Factor (VPF/VEGF) and its Receptors in Human Skin," J. Invest. Dermatol., 108(3):263-268.
Dobrogowska et al., 1998, "Increased Blood-Brain Barrier Permeability and Endothelial Abnormalities Induced by Vascular Endothelial Growth Factor," Journal of Neurocytology, 27:163-173.
Doldi et al., 1996, "Vascular Endothelial Growth Factor—Expression in Human Vulvar Neoplastic and Nonneoplastic Tissues," The Journal of Reproductive Medicine, 41(11):844-848.
Dor and Keshet, 1997, "Ischemia-Driven Angiogenesis," Trends in Cardiovascular Med., 7:289-294.
Feigin and Budzilovich, 1978, "The role of edema in diffuse sclerosis and other leukoencephalopathies," J. Neuropathol. Exp. Neurol., 37:326-357.
Ferrara et al., 1987, "Pituitary Follicular Cells Produce Basic Fibroblast Growth Factor," Proc. Natl. Acad. Sci. USA, 84(16):5773-5777.
Ferrara et al., 1989, "Pituitary Follicular Cells Secrete a Novel Heparin-Binding Growth Factor Specific for Vascular Endothelial Cells," Biochem. Biophys. Res. Commun., 161(2):851-858.
Ferrara et al., 1991, "The Vascular Endothelial Growth Factor Family of Polypeptides," J. Cell Biochem., 47(3):211-218.
Ferrara et al., 1992, "Molecular and Biological Properties of the Vascular Endothelial Growth Factor Family of Proteins," Endocr. Rev., 13(1)18-32.
Ferrara et al., 1997, "The Biology of Vascular Endothelial Growth Factor," Endocr. Rev., 18(1):4-25.
Ferrara et al., 1998, "Vascular Endothelial Growth Factor is Essential for Corpus Luteum Angiogenesis," Nature Medicine, 4(3):336-340.
Fischer et al., 1998, "Barbituates decrease the expression of vascular endothelial growth factor in hypoxic cultures of porcine brain derived microvascular endothelial cells," Molecular Brain Research, 60:89-97.
Folkman et al., 1987, "Angiogenic factors," Science 235:442-447.
Folkman et al., 1989, "Induction of Angiogenesis During the Transition from Hyperplasia to Neoplasia," Nature, 339(6219):58-61.
Gass, 1997, "Stereoscopic atlas of macular diseases diagnosis and treatment," vol. One, Fourth Edition, Mosby, Inc., 1987, pp. 70-87.
Goldman et al., 1993, "Epidermal growth factor stimulates vascular endothelial growth factor production by human malignant glioma cells: A model of glioblastoma multiforme pathophysiology," Molecular Biology of the Cell., 4:121-133.
Goldman et al., 1997, "Brian edema in meningiomas is associated with increased vascular endothelial growth factor expression," Neurosurgery, 40(6):1269-1277.
Goldman et al., 1998, "Paracrine expression of a native soluble vascular endothelial growth factor receptor inhibits tumor growth, metastasis, and mortality rate," Proc. Natl. Acad. Sci. USA., 95:8795-8800.
Gossmann et al., 2002, "Dynamic Contrast-Enhanced Magnetic Resonance Imaging as a Surrogate Marker of Tumor Response to Anti-Angiogenic Therapy in a Xenograft Model of Glioblastoma Multiforme," Journal of Magnetic Resonance Imaging, 15:233-240.
Gridley et al., 1997, "Enhancement of Prostate Cancer Xenograft Growth with Whole-Body Radiation and Vascular Endothelial Growth Factor," Anticancer Research, 17(2a):923-928.
Harlow and Lane, 1988, "Antibodies: A Laboratory Manual," Cold Spring Laboratory, p. 597.
Hayashi et al., 1997, "Rapid Induction of Vascular Endothelial Growth Factor Gene Expression After Transient Middle Cerebral Artery Occlusion in Rats," Stroke, 28(10):2039-2044.
Hayashi et al., 1998, "Reduction of Ischemic Damage by Application of Vascular Endothelial Growth Factor in Rat Brain After Transient Ischemia," J. Cereb. Blood Flow Metab., 18(8):887-895.
Heo et al., 2005, "Fee radicals as triggers of brain edema formation after stroke," Free Radic. Biol, Med., 39:51-70.
Hetian et al., 2002, "A novel peptide isolated from a phage display library inhibits tumor growth and metastasis by blocking the binding of vascular endothelial growth factor to its kinase domain receptor," The Journal of Biological Chemistry, 277(2):43137-43142.
Houck et al., 1991, "The Vascular Endothelial Growth Factor Family: Identification of a Fourth Molecular Species and Characterization of Alternative Splicing of RNA," Mol. Endocrinol, 5(12):1806-1814.
Huang et al., 2001, "Highly specific antiangiogenic therapy is effective in suppressing growth of experimental Wilms tumors," J Pediatr Surg., 36(2):357-361.
Hussain et al., 2008, "Cheiradone: a vascular endothelial cell growth factor receptor antagonist," BMC Cell Biology, 9:7.

Ishikawa et al., 1989, "Identification of Angiogenic Activity and the Cloning and Expression of Platelet-Derived Endothelial Cell Growth Factor," Nature, 338(6216):557-562.

Kakeji et al., 1997, "Dynamics of Tumor Oxygenation, CD31 Staining and Transforming Growth Factor-β Levels After Treatment with Radiation or Cyclophosphamide in the Rat 13762 Mammary Carcinoma," Int. J. Radiation Oncology Biol. Phys., 37(5):1115-1123.

Kalkanis et al., 1996, "Correlation of vascular endothelial growth factor messenger RNA expression with peritumoral vasogenic cerebral edema in meningiomas," J. Neurosurg., 85:1095-1101.

Katoh et al., 1995, "Expression of the Vascular Endothelial Growth Factor (VEGF) Receptor Gene, KDR, in Hematopoietic Cells and Inhibitory Effect of VEGF on Apoptotic Cell Death Caused by Radiation," Cancer Research, 55:5687-5692.

Keck et al., 1989, "Vascular Permeability Factor, an Endothelial Cell Mitogen Related to PDGF," Science, 246(4935):1309-1312.

Kempski, 2001, "Cerebral Edema," Seminars in Nephrology, 21(3):303-307.

Kim et al., 1989, "Epitopes on the S1 Subunit of Pertussis Toxin Recognized by Monoclonal Antibodies," Infection and Immunity, 57:944-950.

Kim et al., 1992, "The vascular endothelial growth factor proteins: Identification of biologically relevant regions by neutralizing monoclonal antibodies," Growth Factors 7:53-64.

Kim et al., 1993, "Inhibition of vascular endothelial growth factor-induced angiogenesis suppresses tumor growth in vivo," Nature, 363:841-844.

Kitamoto et al., 1997, "Vascular endothelial growth factor is an essential molecule for mouse kidney development: Glomerulogenesis and nephrogenesis," J. Clin. Invest. 99: 2351-2357.

Klatzo et al., 1984, "Concepts of Ischemic Injury Associated with Brain Edema," In: Brain Edema, Tokyo Springer, pp. 1-5.

Koochekpour et al., 1995, "Expression of vascular endothelial growth factor in the cyst fluid of human cerebral gliomas," Oncology Reports, 2:1147-1149.

Kovacs et al., 1996, "VEGF and flt: Expression Time Kinetics in Rat Brain Infarct," Stroke, 27(10):1865-1873.

Lee et al., 2004, "1,2,3,4,6-Penta-O-galloyl-beta-D-glucose blocks endothelial cell growth and tube formation through inhibition of VEGF binding to VEGF receptor," Cancer Letters, 208:89-94.

Lee et al., 2005, "Sanguiin H-6 blocks endothelial cell growth through inhibition of VEGF binding to VEGF receptor," Arch. Pharm. Res., 28:1270-1274.

Lennmyr et al., 1998, "Expression of Vascular Endothelial Growth Factor (VEGF) and its Receptors (Flt-1 and Flk-1) Following Permanent and Transient Occlusion of the Middle Cerebral Artery in the Rat," J. Neuropathol. Exp. Neurol., 57(9):874-882.

Leung et al., 1989, "Vascular Eudothelial Growth Factor is a Secreted Angiogenic Mitogen," Science, 246(4935):1306-1309.

Leung et al., 1992, "Cloning, Expression During Development, and Evidence for Release of a Trophic Factor for Ciliary Ganglion Neurons," Neuron, 8(6):1045-1053.

Levy et al., 1996, "Hypoxia-inducible Protein Binding to Vascular Endothelial Growth Factor mRNA and Its Modulation by the von Hippel- Lindau Protein," J. Biol. Chem., 271(41):25492-25497.

Li et al., 1991, "Monoclonal antibodies to recombinant human vascular endothelial growth factor (rHuVEGF)," J. Cellular Biochem. SUPPL No. 15F, p. 251.

Lucas et al., 1996, "High-Level Production of Recombinant Proteins in CHO Cells Using a Dicistronic DHFR Intron Expression Vector," Nucleic Acids Res., 24(9):1774-1779.

Lyttle et al., 1994, "Homologs of Vascular Endothelial Growth Factor Are Encoded by the Poxvirus Orf Virus," J. Virol., 68(1):84-92.

Marti et al., 2000, "Hypoxia-induced vascular endothelial growth factor expression precedes neovascularization after cerebral ischemia," Am. J. Pathol. 156:965-976.

Matthews et al., 1991, "A Receptor Tyrosine Kinase cDNA Isolated from a Population of Enriched Primitive Hematopoietic Cells and Exhibiting Close Genetic Linkage to c-kit," Froc. Natl. Acad. Sci. USA, 88(20).9026-9030.

Megyesi et al., 1990, Journal of Cell Biol., vol. 111(5 Part 2), 227A, Abstract#1267.

Meigs Syndrome, 2006, Wikipedia encyclopedia, Nov. 20, 2006, http://en.wikipedia.org/wiki/Meigs_syndrome.

Miller et al., 1994, "Vascular Endothelial Growth Factor/Vascular Permeability Factor Is Temporally and Spatially Correlated with Ocular Angiogenesis in a Primate Model," Am. J. Pathol., 145(3):574-584.

Mitola et al., 1997, "Tat-Human Immunodeficiency Virus-I Induces Human Monocyte Chemotaxis by Activation of Vascular Endothelial Growth Factor Receptor-1," Blood, 90(4):1365-1372.

Monacci et al., 1993, "Expression of Vascular Permeability FactorNascular Endothelial Growth Factor in Normal Rat Tissues," Am. J. Physiol., 264(4)(Part 1):C995-C1002.

Murata et al., 1995, "Vascular Endothelial Growth Factor Plays a Role in Hyperpermeability of Diabetic Retinal Vessels," Ophthalmic Res., 27:48-52.

Murata et al., 1996, "The Relation between Expression of Vascular Endothelial Growth Factor and Breakdown of the Blood-Retinal Barrier in Diabetic Rat Retinas," Laboratory Investigation, 74(4):819-825.

Nauck et al., 1998, Corticosteroids inhibit the expression of the vascular endothelial growth factor gene in human vascular smooth muscle cells, EP Journ. Of Pharmacol., 341:309-315.

Neufeld et al., 1994, "Vascular Eudothelial Growth Factor and its Receptors," Prog. Growth Factor Res., 5(1):89-97.

Ozaki et al., 1997, "Intravitreal Sustained Release of VEGF Causes Retinal Neovascularization in Rabbits and Breakdown of the Blood-Retinal Barrier in Rabbits and Primates," Exp. Eye Res., 64:505-517.

Phillips et al., 1991, "An Angiogenic Extract from Skeletal Muscle Stimulates Monocyte and Endothelial Cell Chemotaxis In Vitro," Proc. Soc. Exp. Biol. Med., 197:458.

Piossek et al., 1999, "Vascular endothelial growth factor (VEGF) receptor II-derived peptides inhibit VEGF," The Journal of Biological Chemistry, 274:5612-5619.

Provias et al., 1997, "Meningiomas: Role of vascular endothelial growth factor/vascular permeability factor in angiogenesis and peritumoral edema," Neurosurgery, 40(5):1016-1023.

Quam et al., 2001. "VEGF-initiated blood-retinal barrier breakdown in early diabetes" Investigative Ophthalmology and Visual Science 42:2408-2413.

Quinn et al., 1993, "Fetal Liver Kinase I is a Receptor for Vascular Endothelial Growth Factor and is Selectively Expressed in Vascular Endothelium," Froc. Natl. Acad. Sci. USA, 900 6):7533-7537.

Rosenstein et al., 1998, "Patterns of Brain Angiogenesis after Vascular Endothelial Growth Factor Administration in vitro and in vivo," Proc. Natl. Acad. Sci. USA, 95:7086-7091.

Ruckman et al., 1998, "2'-Fluoropyrimidine Rna-based aptamers to the 165-amino acid form of vascular endothelial growth factor (VEGF165). Inhibition of receptor binding and VEGF-induced vascular permeability through interactions requiring the exon 7-encoded domain," J. Biol. Chem., 273:20556-20567.

Sakurada et al., 1996, "Involvement of Vascular Endothelial Growth Factor in Kaposi's Sacroma Associated with Acquired Immunodeficiency Syndrome," Jpn. J. Cancer Res., 87:1143-1152.

Schilling et al., 1999, "Mediators of Cerebral Edema," Adv. Exp. Med. Biol., 474:123-141.

Severinghaus, 1995, "Hypothesis: Angiogenesis cytokines in high altitude cerebral oedema," Acta Anaesthesiol. Scanda., 39(Supplement 107):177-178.

Shibuya et al., 1990, "Nucleotide Sequence and Expression of a Novel Human Receptor-Type Tyrosine Kinase Gene (flt) Closely Related to the fms Family," Oncogene, 5(4):519-524.

Shweiki et al., 1992, "Vascular endothelial growth factor induced by hypoxia may mediate hypoxia-initiated angiogenesis," Nature, 359:843-845.

Shweiki et al., 1992, "Vascular Endothelial Growth Factor Induced by Hypoxia may Mediate Hypoxia-Initiated Angiogenesis," Nature, 359(6398):843-845.

Simard et al., 2007, "Brain oedema in focal ischaemia: molecular pathophysiology and theoretical implications," Lancet Neurol., 6(3):258-268.

Skobe et al., 1997, Halting angiogenesis suppresses carcinoma cell invasion, Nature Medicine, 3(11):1222-1227.

Stone et al., 1995, "Development of Retinal Vasculature is Mediated by Hypoxia-Induced Vascular Endothelial Growth Factor (VEGF) Expression by Neuroglia," J. Neurosci., 15(7, Part 1):4738-4747.

Strugar et al., 1994, "Vascular permeability factor in brain metastases: correlation with vasogenic brain edema and tumor angiogenesis," J. Neurosurg., 81 :560-566.

Takahashi et al., 1991, "Inhibition of brain glutamine accumulation prevents cerebral edema in hyperammonemic rats," Am. J. Physiol. Heart Circ. Physiol., 261:H825-H829.

Terman et al., 1991, "Identification of a New Endothelial Cell Growth Factor Receptor Tyrosine Kinase," Oncogene, 6(9):1677-1683.

Terman et al., 1992, "Identification of the KDR Tyrosine Kinase as a Receptor for Vascular Endothelial Cell Growth Factor," Biochem. Biophys. Res. Commun., 187(3):1579-1586.

Thompson et al., 1991, "Supernatants of Acquired Immunodeficiency Syndrome-Related Kaposi's Sarcoma Cells Induce Endothelial Cell Chemotaxis and Invasiveness," Cancer Res., 51(10):2670-2676.

Tietjen et al., 1996, "Treatment modalities for hypertensive patients with intracranial pathology; options and risks" Crit. Care Med., 24:311-322.

Tischer et al., 1989, "Vascular Endothelial Growth Factor: A New Member of the Platelet-Derived Growth Factor Gene Family," Biochem. Biophys. Res. Commun., 165(3):1198-1206.

Tolentino et al., 1996, "Intravitreous Injections of Vascular Endothelial Growth Factor Produce Retinal Ischemia and Microangiopathy in an Adult Primate," Ophthalmology, 103(10:1820-1828.

Tolentino et al., 1996, "Vascular Endothelial Growth Factor Is Sufficient to Produce Iris Neovascularization and Neovascular Glaucoma in a Nonhuman Primate," Arch. Ophthalmol., 114:964-970.

Tuder and Voelkel, 1998, "Pulmonary hypertension and inflammation," J. Lab. Clin. Med., 132(1):16-24.

Ueno et al., 1991, "Inhibition of PDGF Beta receptor signal transduction by coexpression of a truncated receptor," Science 252:844-848.

Vaquero et al., 2000, "Expression of vascular permeability factor in glioblastoma specimens: correlation with tumor vascular endothelial surface and peritumoral edema,", Journal of Neuro-Oncology, 49:49-55.

Vinores et al., 1997, "Upregulation of vascular endothelial growth factor in ischemic and non-ischemic human and experimental retinal disease," Histol and Histopathol, 12:99-109.

Voelkel et al., 1996, "Vascular Endothelial Growth Factor in Pulmonary Hypertension," Ann. NY Acad. Sci., 796:186-193.

Voelkel et al., 1998, "Primary Pulmonary Hypertension Between Inflammation and Cancer," Chest, 1 14(Supplement):225S-230S.

Waltenberger et al., 1994, "Different Signal Transduction Properties of KDR and Fltl, Two Receptors for Vascular Endothelial Growth Factor," J. Biol. Chem., 269(43):26988-26995.

Weidner et al., 1991, "Tumor Angiogenesis and Metastasis—Correlation in Invasive Breast Carcinoma," N. Engl. J. Med., 324(1):1-8.

Weindel et al., 1994, "Detection and Quantification of Vascular Endothelial Growth Factor/Vascular Permeability Factor in Brain Tumor Tissue and Cyst Fluid: The Key to Angiogenesis?" Neurosurgery, 35(3):439-448.

White et al., 1997, "VEGF mRNA is Stabilized by Ras and Tyrosine Kinase Oncogenes, as well as by UV Radiation-Evidence for Divergent Stabilization Pathways," Growth Factors, 14:199-212.

Xu et al., 1998, "Expression and response to hypoxia of vascular endothelial growth factor (VEGF) in rat and rabbit tissues," Oxygen Transport to Tissue XX, edited by Hudetz and Bruley, Plenum Press, NY, pp. 311-317.

Xu et al., 1998, "Rat brain VEGF expression in alveolar hypoxia: possible role in high-altitude cerebral edema," J. Appl. Physiol., 85:53-57.

Yamada et al., 1993, "Pathophysiology of brain edema and treatment with glucocorticoids," Mol. Med., 30(5):602-610 (in Japanese with English abstract).

Yarmush et al., 1980, "Identification and Characterization of Rabbit-Mouse Hybridomas Secreting Rabbit Immunoglobulin Chains," Proc. Natl. Acad. Sci. USA, 77(5):2899-2903.

Yelton et al., 1978, "Fusion of Mouse Myeloma and Spleen Cells," Curr. Top Microbiol. Immunol., 81:1-7.

Zhao, L. et al., 1998 "Effects of vascular permeability factor on the permeability of cultured endothelial cells from brain capillaries" Journal of Cardiovascular Pharmacology, 32(1): 1-4.

Zilberberg et al., 2003, "Structure and inhibitory effects on angiogenesis and tumor development of a new vascular endothelial growth inhibitor," The Journal of Biological Chemistry, 278(37):35564-35573.

U.S. Appl. No. 10/683,043, Office Action mailed Jul. 11, 2006.

U.S. Appl. No. 10/683,043, Office Action mailed Mar. 12, 2007.

U.S. Appl. No. 10/683,043, Office Action mailed Oct. 19, 2007.

EP application No. 02006351, Copy of Partial European Search Report dated Aug. 22, 2002.

EP application No. 05075989.3, Copy of European Search Report dated Aug. 4, 2005.

International Preliminary Examination Report for International Application No. PCT/US99/29475, mailed Jan. 4, 2001.

International Search Report for International Application No. PCT/US92/09218, mailed Jul. 8, 1993.

Jun. 26, 2006 European Opposition Matters.

* cited by examiner

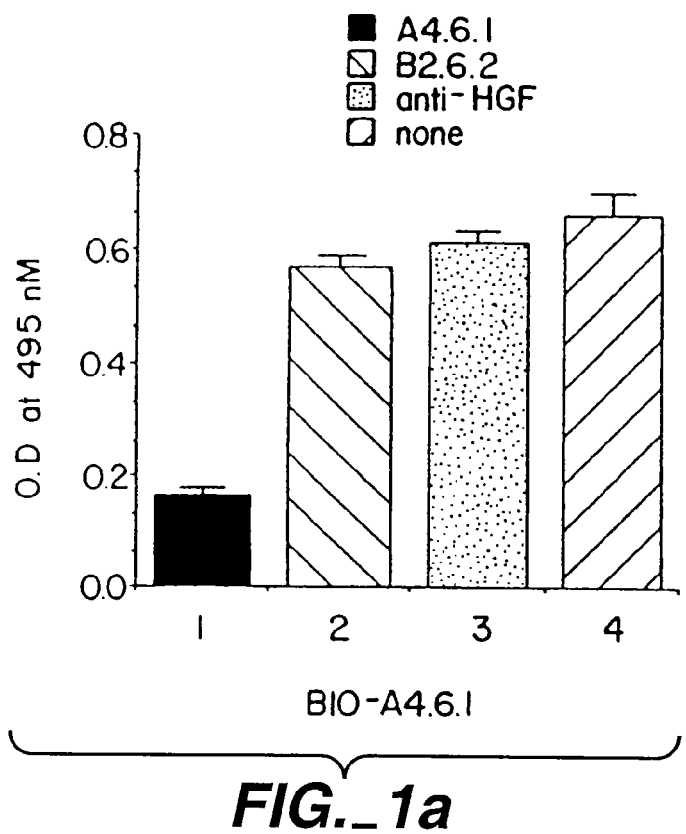
FIG._1a
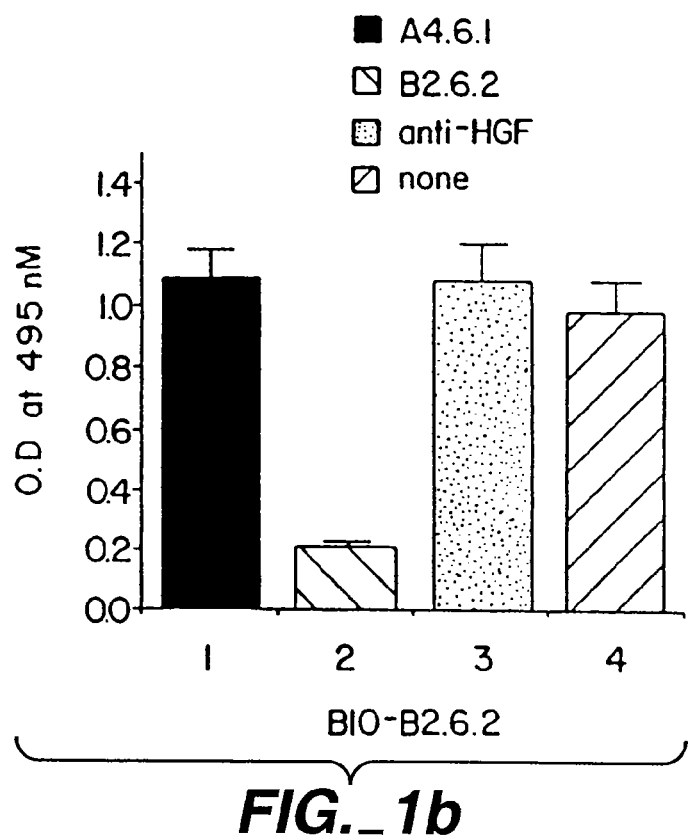
FIG._1b

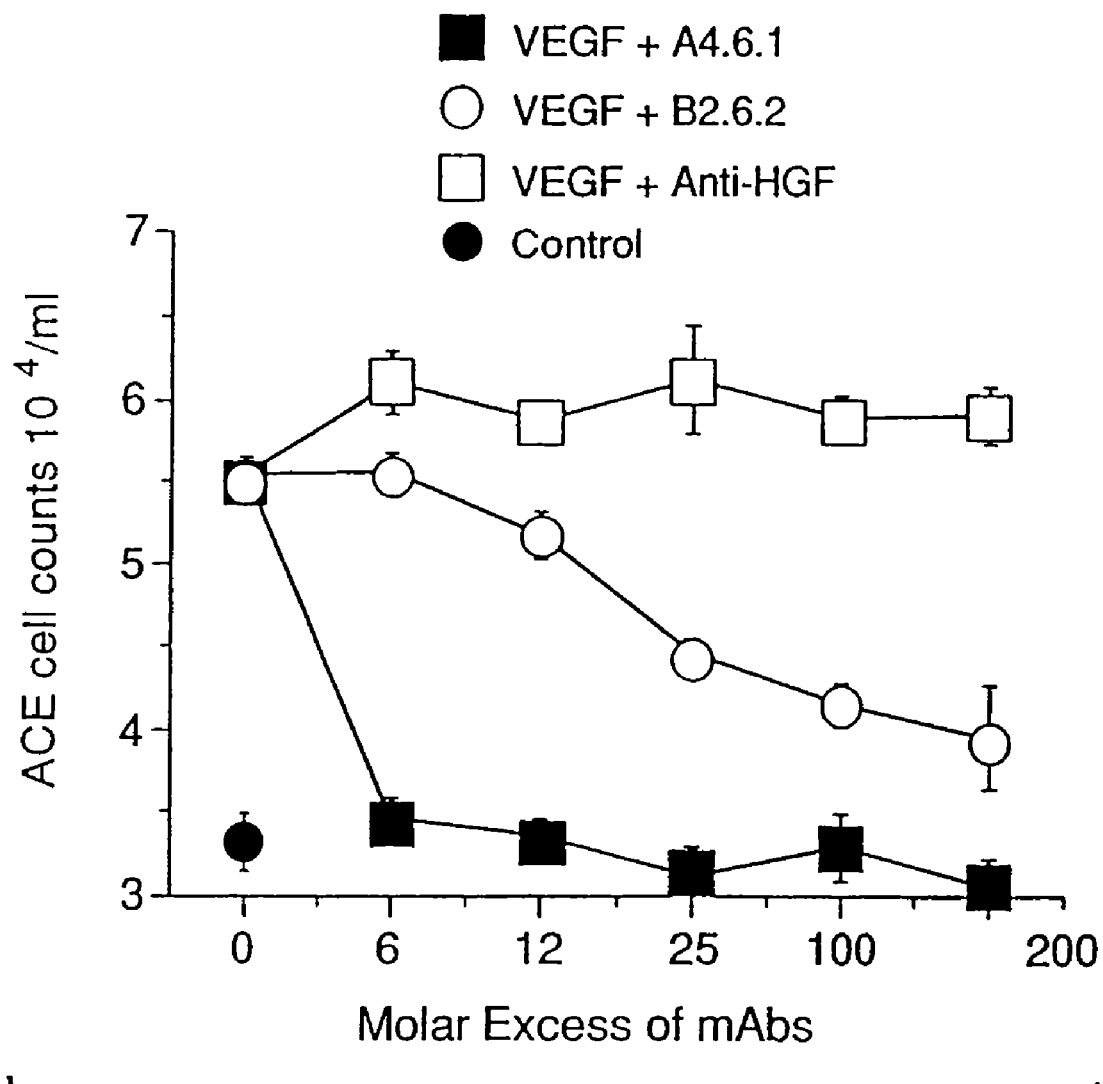
FIG._2

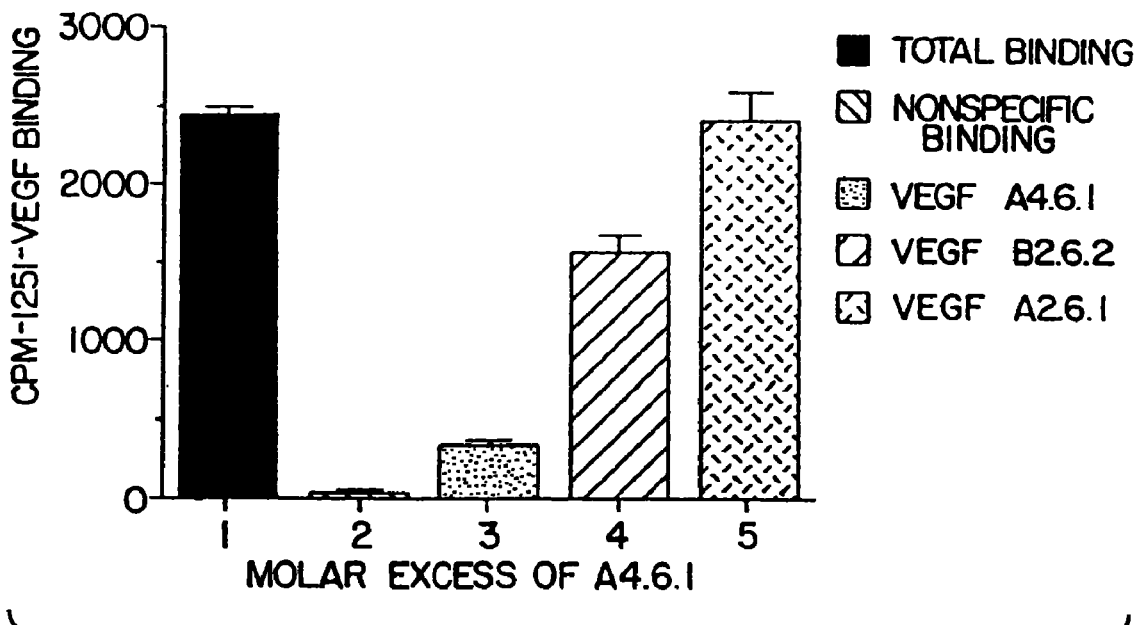
FIG._3a
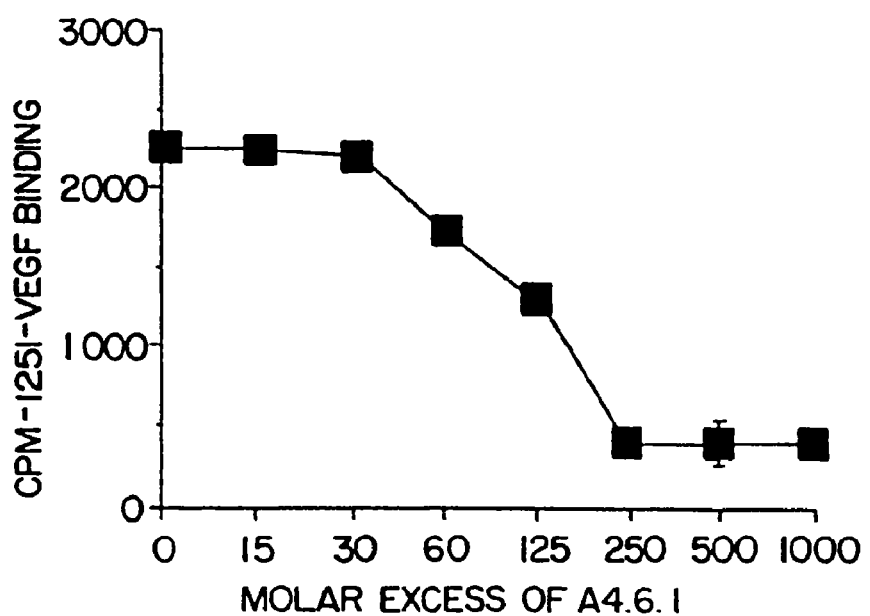
FIG._3b

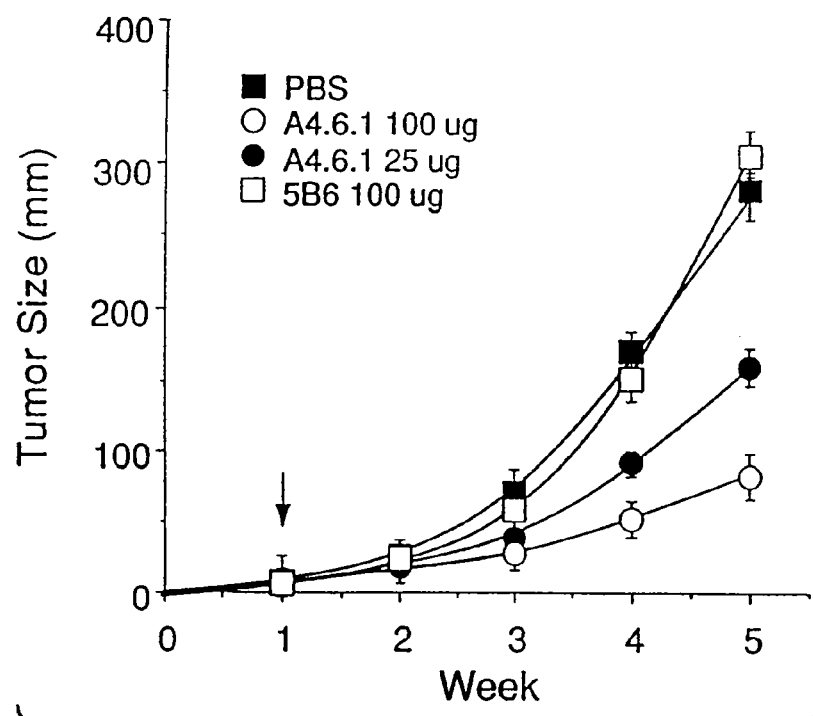
FIG._4
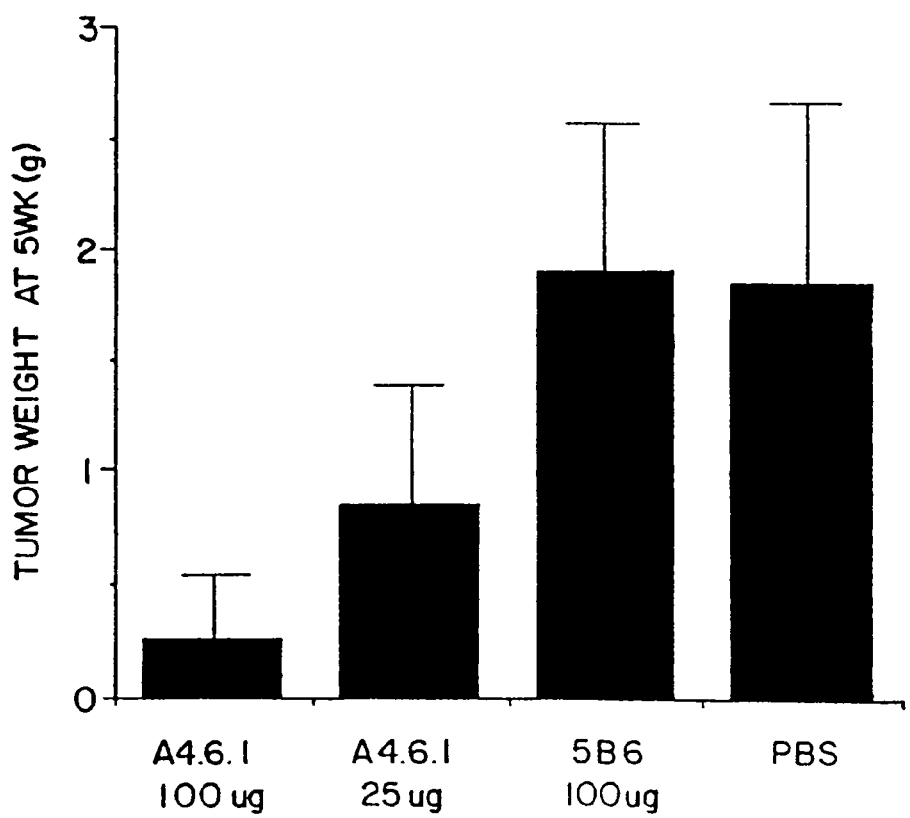
FIG._5

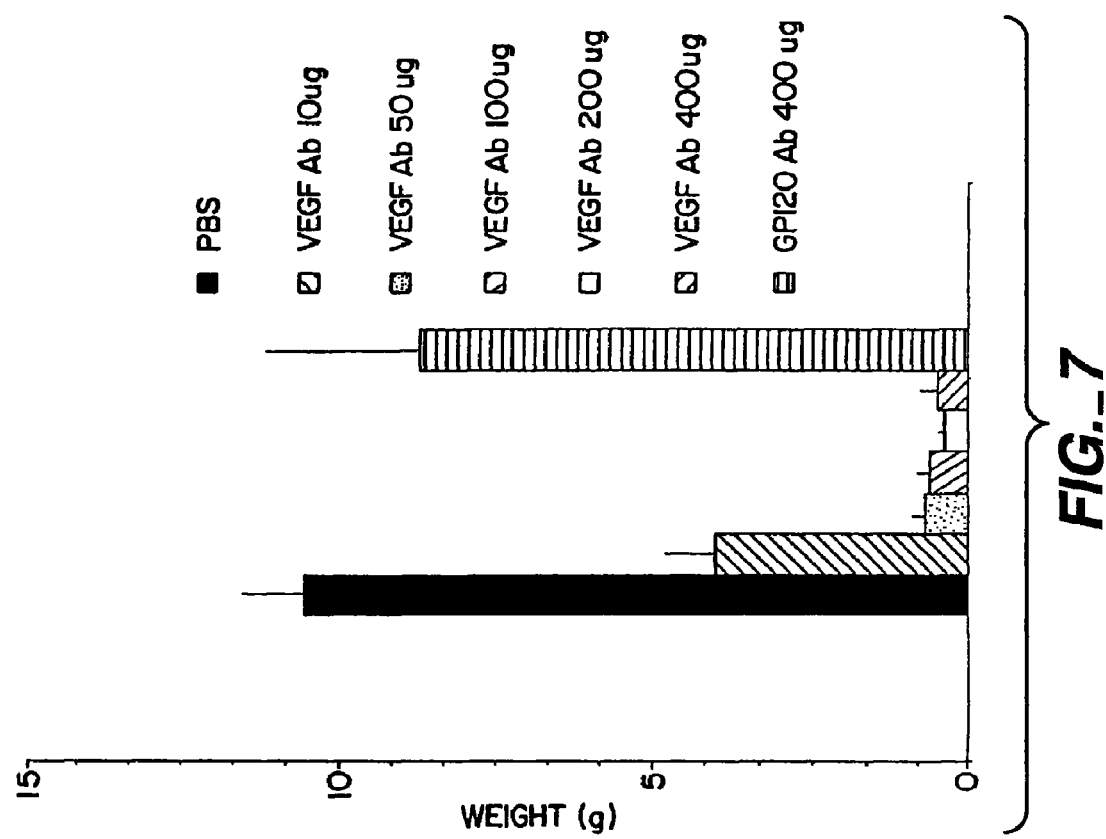
FIG._7
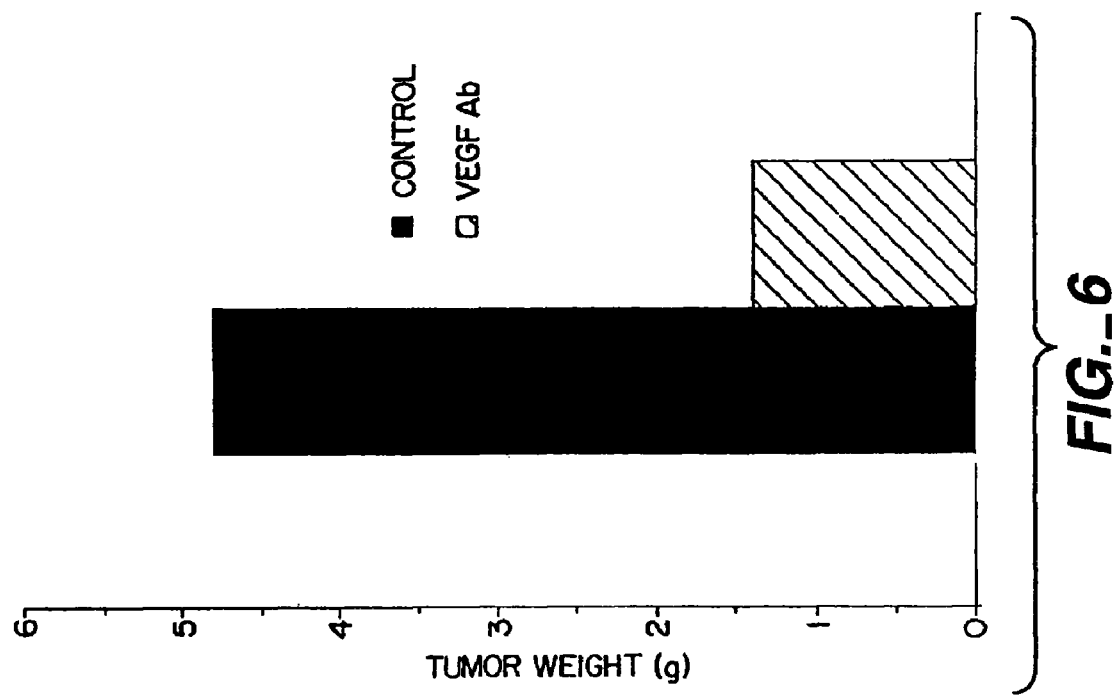
FIG._6

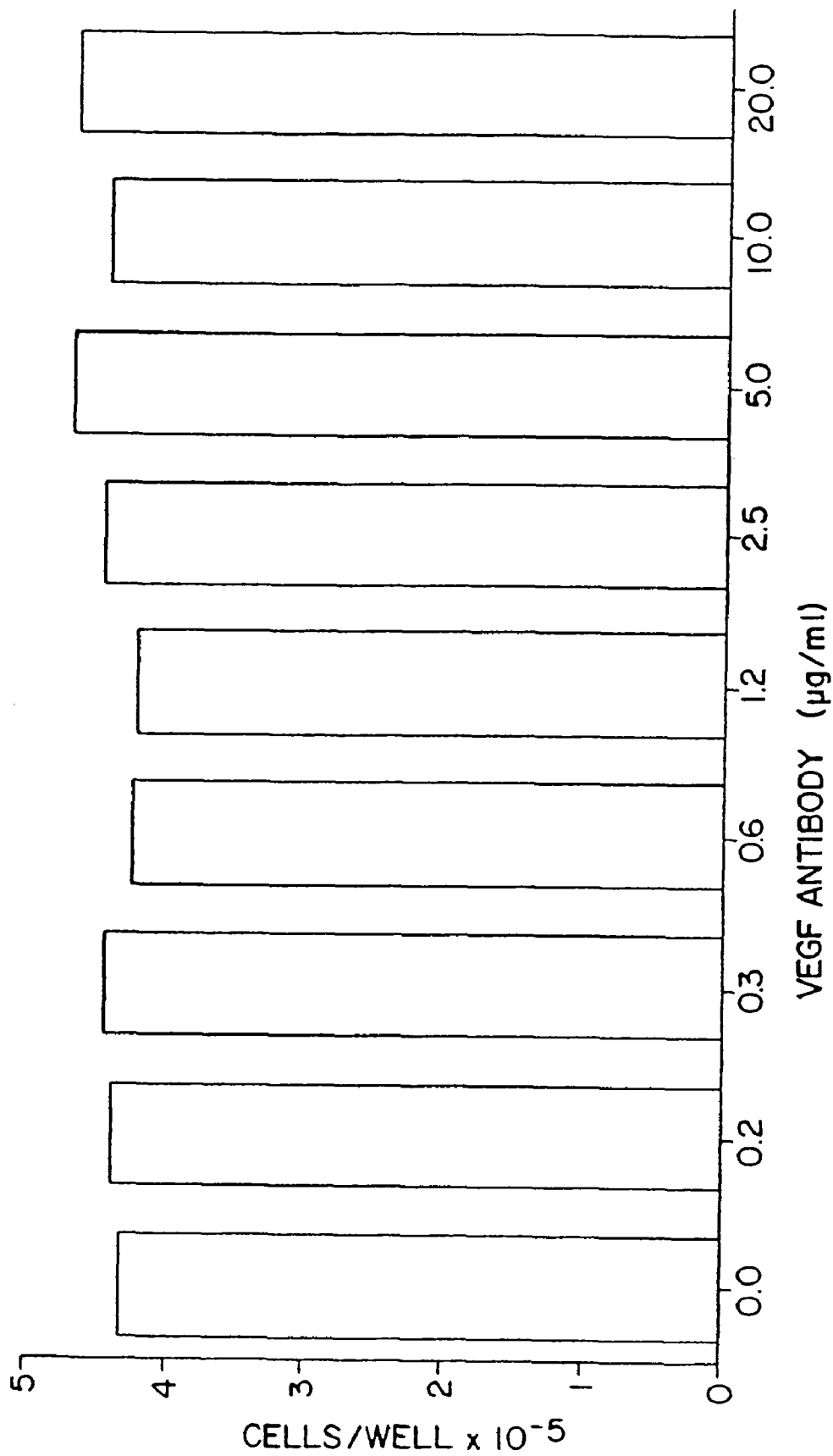

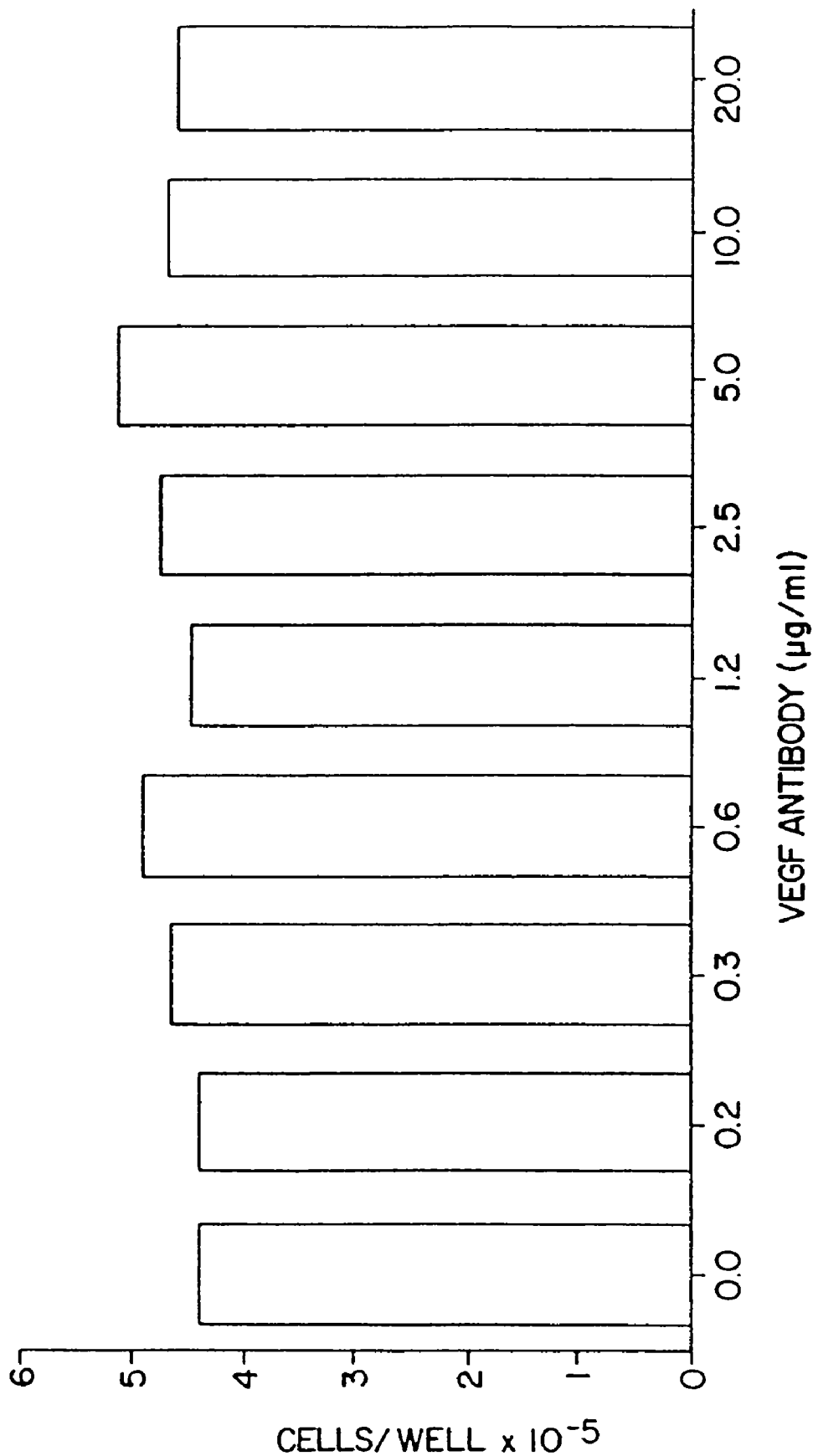
FIG._9

| Sample Type | Sample # | Assay Date | Syn. Fluid | Syn. Fluid + mAB VEGF | % Suppression |
|---|---|---|---|---|---|
| Rheumatoid Syn. Fluid | 318 | 5.7.92 | 5.2 ± 0.2 | 2.7 ± 0.3 | 48 |
| | 150 | 5.7.92 | 7.0 ± 0.3 | 2.8 ± 0.4 | 60 |
| | 312 | 5.7.92 | 6.7 ± 0.4 | 3.7 ± 0.3 | 45 |
| | 264 | 5.7.92 | 6.2 ± 0.4 | 3.1 ± 0.3 | 50 |
| | 267 | 5.7.92 | 5.7 ± 0.6 | 4.4 ± 0.3 | 23 |
| | 202 | 5.22.92 | 10.0 ± 0.5 | 3.4 ± 0.6 | 66 |
| | 314 | 5.22.92 | 7.5 ± 0.3 | 3.1 ± 0.6 | 59 |
| | 237 | 5.22.92 | 6.1 ± 0.5 | 2.2 ± 0.3 | 64 |
| | 206 | 5.22.92 | 6.7 ± 0.5 | 2.2 ± 0.3 | 67 |
| | 317 | 5.22.92 | 5.2 ± 0.3 | 2.5 ± 0.6 | 52 |
| Osteoarthritis Syn. Fluid | 165 | 6.2.92 | 4.0 ± 0.3 | 2.8 ± 0.4 | 30 |
| | 211 | 6.2.92 | 3.4 ± 0.5 | 3.0 ± 0.2 | 11.7 |
| | 195 | 6.2.92 | 3.5 ± 0.2 | 3.3 ± 0.3 | 5.7 |
| | 122 | 6.2.92 | 3.7 ± 0.3 | 3.2 ± 0.4 | 13.5 |
| | 16 | 6.2.92 | 4.1 ± 0.3 | 3.8 ± 0.5 | 7.3 |

Mean % Suppression for RA Fluids 53.4 4.2
Mean % Suppression for OA Fluids 13.6 3.9
Synovial fluids were diluted 1:50.

Controls:

| | | | |
|---|---|---|---|
| 6.2.92 | PBS | 3.3 | 0.30 |
| | bFGF 1μg/ml | 3.7 | 0.38 |
| 5.22.92 | PBS | 1.2 | 0.38 |
| | bFGF 1μg/ml | 7.8 | 0.31 |
| 5.2.92 | PBS | 1.3 | 0.18 |
| | bFGF 1μg/ml | 9.0 | 0.41 |

*FIG. 10*

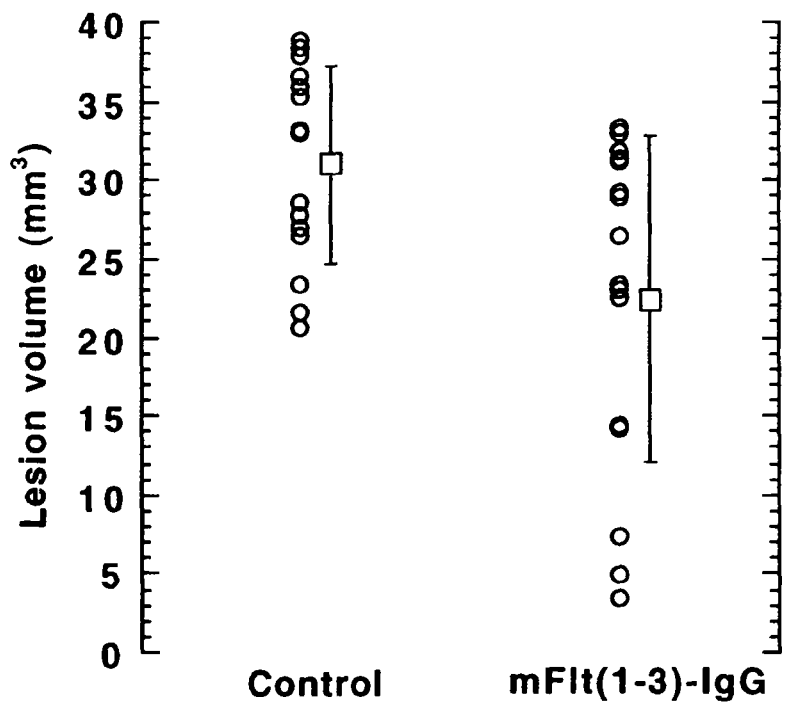
FIG._11
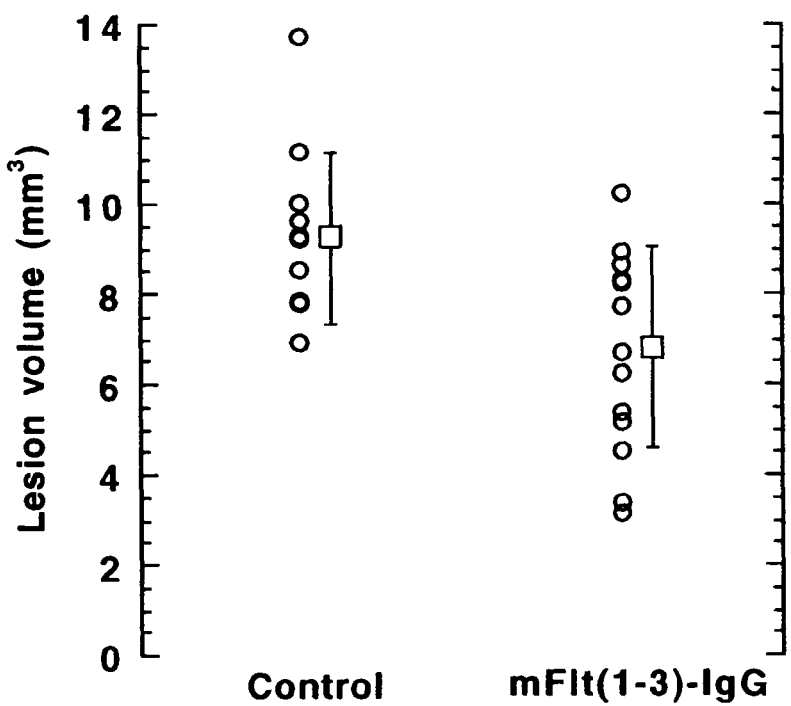
FIG._13

FIG._12

```
           10          20          30         40
F(ab)-12   DIQMTQSPSS  LSASVGDRVT  ITCSASQDIS NYLNWYQQKP
Y0243-1    DIQLTQSPSS  LSASVGDRVT  ITCRANEQLS NYLNWYQQKP
Y0238-3    DIQLTQSPSS  LSASVGDRVT  ITCRANEQLS NYLNWYQQKP
Y0313-1    DIQLTQSPSS  LSASVGDRVT  ITCRANEQLS NYLNWYQQKP
Y0317      DIQLTQSPSS  LSASVGDRVT  ITCSASQDIS NYLNWYQQKP
                                        CDR-L1
           50          60          70         80
F(ab)-12   GKAPKVLIYF  TSSLHSGVPS  RFSGSGSGTD FTLTISSLQP
Y0243-1    GKAPKVLIYF  TSSLHSGVPS  RFSGSGSGTD FTLTISSLQP
Y0238-3    GKAPKVLIYF  TSSLHSGVPS  RFSGSGSGTD FTLTISSLQP
Y0313-1    GKAPKVLIYF  TSSLHSGVPS  RFSGSGSGTD FTLTISSLQP
Y0317      GKAPKVLIYF  TSSLHSGVPS  RFSGSGSGTD FTLTISSLQP
                  CDR-L2
           90         100         110
F(ab)-12   EDFATYYCQQ  YSTVPWTFGQ  GTKVEIKRTV
Y0243-1    EDFATYYCQQ  YSTVPWTFGQ  GTKVEIKRTV
Y0238-3    EDFATYYCQQ  YSTVPWTFGQ  GTKVEIKRTV
Y0313-1    EDFATYYCQQ  YSTVPWTFGQ  GTKVEIKRTV
Y0317      EDFATYYCQQ  YSTVPWTFGQ  GTKVEIKRTV
                  CDR-L3
```

FIG._14A

```
           10          20          30         40
F(ab)-12   EVQLVESGGG  LVQPGGSLRL  SCAASGYTFT NYGMNWVRQA
Y0243-1    EVQLVESGGG  LVQPGGSLRL  SCAASGYDFT HYGMNWVRQA
Y0238-3    EVQLVESGGG  LVQPGGSLRL  SCAASGYTFT NYGINWVRQA
Y0313-1    EVQLVESGGG  LVQPGGSLRL  SCAASGYDFT HYGMNWVRQA
Y0317      EVQLVESGGG  LVQPGGSLRL  SCAASGYDFT HYGMNWVRQA
                                        CDR-H1
           50          60          70         80
F(ab)-12   PGKGLEWVGW  INTYTGEPTY  AADFKRRFTF SLDTSKSTAY
Y0243-1    PGKGLEWVGW  INTYTGEPTY  AADFKRRFTF SLDTSKSTAY
Y0238-3    PGKGLEWVGW  INTYTGEPTY  AADFKRRFTF SLDTSKSTAY
Y0313-1    PGKGLEWVGW  INTYTGEPTY  AADFKRRFTF SLDTSKSTAY
Y0317      PGKGLEWVGW  INTYTGEPTY  AADFKRRFTF SLDTSKSTAY
                  CDR-H2                  CDR-7
           90         100         110
F(ab)-12   LQMNSLRAED  TAVYYCAKYP  HYYGSSHWYF DVWGQGTL
Y0243-1    LQMNSLRAED  TAVYYCAKYP  HYYGSSHWYF DVWGQGTL
Y0238-3    LQMNSLRAED  TAVYYCAKYP  YYYGTSHWYF DVWGQGTL
Y0313-1    LQMNSLRAED  TAVYYCAKYP  YYYGTSHWYF DVWGQGTL
Y0317      LQMNSLRAED  TAVYYCAKYP  YYYGTSHWYF DVWGQGTL
                                 CDR-H3
```

FIG._14B

☐ = differences from F(ab)-12

```
                    10                  20                  30
F(ab)-12  DIQMTQSPSSLSASVGDRVTITCSASQDISNYLNWYQQ
Y0192     DIQLTQSPSSLSASVGDRVTITCRANEQLSNYLNWYQQ
Y0238-3   DIQLTQSPSSLSASVGDRVTITCRANEQLSNYLNWYQQ
Y0239-19  DIQLTQSPSSLSASVGDRVTITCRANEQLSNYLNWYQQ
Y0313-2   DIQLTQSPSSLSASVGDRVTITCRANEQLSNYLNWYQQ
                                      CDR-L1

40        50        60        70
F(ab)-12  KPGKAPKVLIYFTSSLHSGVPSRFSGSGSGTDFTLTIS
Y0192     KPGKAPKVLIYFTSSLHSGVPSRFSGSGSGTDFTLTIS
Y0238-3   KPGKAPKVLIYFTSSLHSGVPSRFSGSGSGTDFTLTIS
Y0239-19  KPGKAPKVLIYFTSSLHSGVPSRFSGSGSGTDFTLTIS
Y0313-2   KPGKAPKVLIYFTSSLHSGVPSRFSGSGSGTDFTLTIS
                     CDR-L2

80        90        100
F(ab)-12  SLQPEDFATYYCQQYSTVPWTFGQGTKVEIKRTV
Y0192     SLQPEDFATYYCQQYSTVPWTFGQGTKVEIKRTV
Y0238-3   SLQPEDFATYYCQQYSTVPWTFGQGTKVEIKRTV
Y0239-19  SLQPEDFATYYCQQYSTVPWTFGQGTKVEIKRTV
Y0313-2   SLQPEDFATYYCQQYSTVPWTFGQGTKVEIKRTV
                     CDR-L3
```

FIG._15A

☐ = differences from F(ab)-12

```
                   10                  20                  30
F(ab)-12   EVQLVESGGGLVQPGGSLRLSCAASGYTFTNYGMNWVR
Y0192      EVQLVESGGGLVQPGGSLRLSCAASGYTFTNYGMNWVR
Y0238-3    EVQLVESGGGLVQPGGSLRLSCAASGY[D]F[TH]YGMNWVR
Y0239-19   EVQLVESGGGLVQPGGSLRLSCAASGYTFTNYGMNWVR
Y0313-2    EVQLVESGGGLVQPGGSLRLSCAASGY[D]F[TH]YGMNWVR
                                        CDR-H1

40              50          60           70
F(ab)-12   QAPGKGLEWVGWINTYTGEPTYAADFKRRFTFSLDTSKSTA
Y0192      QAPGKGLEWVGWINTYTGEPTYAADFKRRFTFSLDTSKSTA
Y0238-3    QAPGKGLEWVGWINTYTGEPTYAADFKRRFTFSLDTSKSTA
Y0239-19   QAPGKGLEWVGWINTYTGEPTYAADFKRRFTFSLDTSKSTA
Y0313-2    QAPGKGLEWVGWINTYTGEPTYAADFKRRFTFSLDTSKSTA
                        CDR-H2

80            90           100
F(ab)-12   YLQMNSLRAEDTAVYYCAKYPHYYG----SSHWYFDVWGQGTL
Y0192      YLQMNSLRAEDTAVYYCAKYPHYYG----SSHWYFDVWGQGTL
Y0238-3    YLQMNSLRAEDTAVYYCAKYPHYYG----SSHWYFDVWGQGTL
Y0239-19   YLQMNSLRAEDTAVYYCAKYPHY[VNERK]SHWYFDVWGQGTL
Y0313-2    YLQMNSLRAEDTAVYYCAKYPHY[VNERK]SHWYFDVWGQGTL
                                    CDR-7        CDR-H3
```

FIG._15B

SEQUENCE LISTING

<160> NUMBER OF SEQ ID NOS: 16

<210> SEQ ID NO 1
<211> LENGTH: 110
<212> TYPE: PRT
<213> ORGANISM: Homo sapiens

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                  100                 105

Ile Lys Arg Thr Val
                110

<210> SEQ ID NO 2
<211> LENGTH: 110
<212> TYPE: PRT
<213> ORGANISM: Homo sapiens

<400> SEQUENCE: 2

Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                  100                 105

Ile Lys Arg Thr Val
                110

<210> SEQ ID NO 3
<211> LENGTH: 110
<212> TYPE: PRT
<213> ORGANISM: Homo sapiens

<400> SEQUENCE: 3

Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser

```
                    20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
               110

<210> SEQ ID NO 4
<211> LENGTH: 110
<212> TYPE: PRT
<213> ORGANISM: Homo sapiens

<400> SEQUENCE: 4

Asp Ile Gln Leu Thr Gln Ser Pro Ser Ser Leu Ser Ala Ser Val
  1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
               110

<210> SEQ ID NO 5
<211> LENGTH: 110
<212> TYPE: PRT
<213> ORGANISM: Homo sapiens

<400> SEQUENCE: 5

Asp Ile Gln Leu Thr Gln Ser Pro Ser Ser Leu Ser Ala Ser Val
  1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105
```

```
Ile Lys Arg Thr Val
                110

<210> SEQ ID NO 6
<211> LENGTH: 110
<212> TYPE: PRT
<213> ORGANISM: Homo sapiens

<400> SEQUENCE: 6

Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
                110

<210> SEQ ID NO 7
<211> LENGTH: 110
<212> TYPE: PRT
<213> ORGANISM: Homo sapiens

<400> SEQUENCE: 7

Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
                110

<210> SEQ ID NO 8
<211> LENGTH: 110
<212> TYPE: PRT
<213> ORGANISM: Homo sapiens

<400> SEQUENCE: 8

Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser
```

```
                    20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
            50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
            95                  100                 105

Ile Lys Arg Thr Val
            110

<210> SEQ ID NO 9
<211> LENGTH: 118
<212> TYPE: PRT
<213> ORGANISM: Homo sapiens

<400> SEQUENCE: 9

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
            35                  40                  45

Glu Trp Val Gly Trp Ile Asn Thr Tyr Thr Gly Glu Pro Thr Tyr
        50                  55                  60

Ala Ala Asp Phe Lys Arg Arg Phe Thr Phe Ser Leu Asp Thr Ser
65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
            95                  100                 105

Ser His Trp Tyr Phe Asp Val Trp Gly Gln Gly Thr Leu
        110                 115

<210> SEQ ID NO 10
<211> LENGTH: 118
<212> TYPE: PRT
<213> ORGANISM: Homo sapiens

<400> SEQUENCE: 10

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Asp Phe Thr
                20                  25                  30

His Tyr Gly Met Asn Trp Val Arg Gln Ala Pro Gly Lys Gly Leu
            35                  40                  45

Glu Trp Val Gly Trp Ile Asn Thr Tyr Thr Gly Glu Pro Thr Tyr
        50                  55                  60

Ala Ala Asp Phe Lys Arg Arg Phe Thr Phe Ser Leu Asp Thr Ser
65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
            95                  100                 105
```

```
Ser His Trp Tyr Phe Asp Val Trp Gly Gln Gly Thr Leu
            110                 115
```

<210> SEQ ID NO 11
<211> LENGTH: 118
<212> TYPE: PRT
<213> ORGANISM: Homo sapiens

<400> SEQUENCE: 11

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Ile Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro Tyr Tyr Tyr Gly Thr
                95                 100                 105

Ser His Trp Tyr Phe Asp Val Trp Gly Gln Gly Thr Leu
            110                 115
```

<210> SEQ ID NO 12
<211> LENGTH: 118
<212> TYPE: PRT
<213> ORGANISM: Homo sapiens

<400> SEQUENCE: 12

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Asp Phe Thr
                20                  25                  30

His Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro Tyr Tyr Tyr Gly Thr
                95                 100                 105

Ser His Trp Tyr Phe Asp Val Trp Gly Gln Gly Thr Leu
            110                 115
```

<210> SEQ ID NO 13
<211> LENGTH: 118
<212> TYPE: PRT
<213> ORGANISM: Homo sapiens

<400> SEQUENCE: 13

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Asp Phe Thr
```

```
                    20                  25                  30

His Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
            50                  55                  60

Ala Ala Asp Phe Lys Arg Arg Phe Thr Phe Ser Leu Asp Thr Ser
            65                  70                  75

Lys Ser Thr Ala Tyr Leu Gln Met Asn Ser Leu Arg Ala Glu Asp
            80                  85                  90

Thr Ala Val Tyr Tyr Cys Ala Lys Tyr Pro Tyr Tyr Tyr Gly Thr
            95                  100                 105

Ser His Trp Tyr Phe Asp Val Trp Gly Gln Gly Thr Leu
            110                 115

<210> SEQ ID NO 14
<211> LENGTH: 118
<212> TYPE: PRT
<213> ORGANISM: Homo sapiens

<400> SEQUENCE: 14

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
            50                  55                  60

Ala Ala Asp Phe Lys Arg Arg Phe Thr Phe Ser Leu Asp Thr Ser
            65                  70                  75

Lys Ser Thr Ala Tyr Leu Gln Met Asn Ser Leu Arg Ala Glu Asp
            80                  85                  90

Thr Ala Val Tyr Tyr Cys Ala Lys Tyr Pro His Tyr Tyr Gly Ser
            95                  100                 105

Ser His Trp Tyr Phe Asp Val Trp Gly Gln Gly Thr Leu
            110                 115

<210> SEQ ID NO 15
<211> LENGTH: 121
<212> TYPE: PRT
<213> ORGANISM: Homo sapiens

<400> SEQUENCE: 15

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
            50                  55                  60

Ala Ala Asp Phe Lys Arg Arg Phe Thr Phe Ser Leu Asp Thr Ser
            65                  70                  75

Lys Ser Thr Ala Tyr Leu Gln Met Asn Ser Leu Arg Ala Glu Asp
            80                  85                  90

Thr Ala Val Tyr Tyr Cys Ala Lys Tyr Pro His Tyr Tyr Val Asn
            95                  100                 105
```

```
Glu Arg Lys Ser His Trp Tyr Phe Asp Val Trp Gly Gln Gly Thr
                110                 115                 120

Leu

<210> SEQ ID NO 16
<211> LENGTH: 121
<212> TYPE: PRT
<213> ORGANISM: Homo sapiens

<400> SEQUENCE: 16

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Asp Phe Thr
                 20                  25                  30

His Tyr Gly Met Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Phe Ser Leu Asp Thr Ser
                 65                  70                  75

Lys Ser Thr Ala Tyr Leu Gln Met Asn Ser Leu Arg Ala Glu Asp
                 80                  85                  90

Thr Ala Val Tyr Tyr Cys Ala Lys Tyr Pro His Tyr Tyr Val Asn
                 95                 100                 105

Glu Arg Lys Ser His Trp Tyr Phe Asp Val Trp Gly Gln Gly Thr
                110                 115                 120

Leu
```

VASCULAR ENDOTHELIAL CELL GROWTH FACTOR ANTAGONISTS AND USES THEREOF

This application is a continuation under 37 CFR §1.53(b) of U.S. application Ser. No. 10/683,043, filed Oct. 9, 2003 (now abandoned), which is a continuation of U.S. application Ser. No. 09/218,481, filed Dec. 22, 1998 (now abandoned), the disclosures of which are incorporated herein by reference herein in their entirety.

FIELD OF THE INVENTION

The present invention relates to vascular endothelial cell growth factor (VEGF) antagonists, to therapeutic compositions comprising the antagonists, and to methods of use of the antagonists for diagnostic and therapeutic purposes. In particular, the present invention relates to methods of treatment of stroke or edema using VEGF antagonists.

BACKGROUND OF THE INVENTION

The two major cellular components of the vasculature are the endothelial and smooth muscle cells. The endothelial cells form the lining of the inner surface of all blood vessels, and constitute a nonthrombogenic interface between blood and tissue. In addition, endothelial cells are an important component for the development of new capillaries and blood vessels. Thus, endothelial cells proliferate during the angiogenesis, or neovascularization, associated with tumor growth and metastasis, as well as a variety of non-neoplastic diseases or disorders.

Various naturally occurring polypeptides reportedly induce the proliferation of endothelial cells. Among those polypeptides are the basic and acidic fibroblast growth factors (FGF), Burgess and Maciag, Annual Rev. Biochem., 58:575 (1989), platelet-derived endothelial cell growth factor (PD-ECGF), Ishikawa, et al., Nature, 338:557 (1989), and vascular endothelial growth factor (VEGF), Leung, et al., Science 246:1306 (1989); Ferrara & Henzel, Biochem. Biophys. Res. Commun. 161:851 (1989); Tischer, et al., Biochem. Biophys. Res. Commun. 165:1198 (1989); Ferrara, et al., PCT Pat. Pub. No. WO 90/13649 (published Nov. 15, 1990).

VEGF was first identified in media conditioned by bovine pituitary follicular or folliculostellate cells. Biochemical analyses indicate that bovine VEGF is a dimeric protein with an apparent molecular mass of approximately 45,000 Daltons, and with an apparent mitogenic specificity for vascular endothelial cells. DNA encoding bovine VEGF was isolated by screening a cDNA library prepared from such cells, using oligonucleotides based on the amino-terminal amino acid sequence of the protein as hybridization probes.

Human VEGF was obtained by first screening a cDNA library prepared from human cells, using bovine VEGF cDNA as a hybridization probe. One cDNA identified thereby encodes a 165-amino acid protein having greater than 95% homology to bovine VEGF, which protein is referred to as human VEGF (hVEGF). The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. See, Leung, et al., Science 246:1306 (1989).

Several additional cDNAs were identified in human cDNA libraries that encode 121-, 189-, and 206-amino acid isoforms of hVEGF (also collectively referred to as hVEGF-related proteins). The 121-amino acid protein differs from hVEGF by virtue of the deletion of the 44 amino acids between residues 116 and 159 in hVEGF. The 189-amino acid protein differs from hVEGF by virtue of the insertion of 24 amino acids at residue 116 in hVEGF, and apparently is identical to human vascular permeability factor (hVPF). The 206-amino acid protein differs from hVEGF by virtue of an insertion of 41 amino acids at residue 116 in hVEGF. Houck, et al., Mol. Endocrin. 5:1806 (1991); Ferrara, et al., J. Cell. Biochem. 47:211 (1991); Ferrara, et al., Endocrine Reviews 13:18 (1992); Keck, et al., Science 246:1309 (1989); Connolly, et al., J. Biol. Chem. 264:20017 (1989); Keck, et al., EPO Pat. Pub. No. 0 370 989 (published May 30, 1990).

Receptors for VEGF have been described in the literature. Two such receptors, flt-1 and flk-1, have been found to mediate VEGF effects [DeVries et al., Science 255:989 (1992); Shibuya et al., Oncogene 5:519 (1990); Matthews et al., Proc. Natl. Acad. Sci. 88:9026 (1991); Terman et al., Oncogene 6:1677 (1991); Terman et al., Biochem. Biophys. Res. Comm. 187:1579 (1992); Neufeld et al., Prog. Growth Factor Res. 5:89-97 (1994); Waltenberger et al., J. Biol. Chem. 269: 26988 (1994); Quinn et al., Proc. Natl. Acad. Sci. 90:7533 (1993)], but their regulation and mechansims are not yet fully understood. Lennmyr et al., J. Neuropathology and Exp. Neurology 57:874-882 (1998). Both the flt-1 and flk-1 receptors are membrane-spanning receptors and belong to the class III tyrosine kinase receptor family. Barleon et al., J. Cell Biochem. 54:56 (1994); Neufeld et al., supra.

VEGF not only stimulates vascular endothelial cell proliferation, but also induces angiogenesis. Angiogenesis, which involves the formation of new blood vessels from preexisting endothelium, is an important component of a variety of diseases and disorders including tumor growth and metastasis, rheumatoid arthritis, psoriasis, atherosclerosis, diabetic retinopathy, retrolental fibroplasia, neovascular glaucoma, age-related macular degeneration, hemangiomas, immune rejection of transplanted corneal tissue and other tissues, and chronic inflammation.

In the case of tumor growth, angiogenesis appears to be crucial for the transition from hyperplasia to neoplasia, and for providing nourishment to the growing solid tumor. Folkman, et al., Nature 339:58 (1989). Angiogenesis also allows tumors to be in contact with the vascular bed of the host which may provide a route for metastasis of the tumor cells. Evidence for the role of angiogenesis in tumor metastasis is provided, for example, by studies showing a correlation between the number and density of microvessels in histologic sections of invasive human breast carcinoma and actual presence of distant metastases. Weidner, et al., New Engl. J. Med. 324:1 (1991).

VEGF has also been reported to be involved in endothelial and vascular permeability. See, Ferrara et al., Endocrine Reviews 18:4-25 (1997); Dobrogowska et al., J. Neurocytology 27:163 (1998). Although not fully understood, VEGF is believed to increase endothelial cell leakage in skin, retina, and tumor tissues. Collins et al., Brit. J. Pharmacology 109: 195 (1993); Connolly et al., J. Clin. Invest. 84:1470 (1989); Shweiki et al., Nature 359:843 (1992); Monacci et al., Am. J. Physiol. 264:C995 (1993); Stone et al., J. Neurosci. 15:4738 (1995); Detmar et al., J. Invest. Dermatol. 108:263 (1997); Weindel et al., Neurosurgery 35:437 (1994). The potential effects and role of VEGF (and its receptors, particularly, the flt-1 receptor), on endothelial cell and blood-brain barrier permeability have also been examined. See, e.g., Rosenstein et al., Proc. Natl. Acad. Sci. 95:7086 (1998); Dobrogowska, supra; Kovacs et al., Stroke 27:1865 (1996). Relatively diffuse VEGF mRNA expression has been observed in adult rat brain but at somewhat low abundance. Monacci et al., Am. J.

Physiol. 146:368-378 (1993). However, reduced oxygen tension has been shown to trigger VEGF expression [Dor and Keshet, Trends in Cardiovascular Med., 7:289-294 (1998)] and enhanced levels of VEGF, flt-1, and flk-1 have been shown to occur in the rat brain following the induction of focal cerebral ischemia. Hayashi et al., Stroke 28:2039 (1997); Kovacs et al., supra; Lennmyr et al., J. Neuropathology and Experimental Neurology, 57:874 (1998). The role of VEGF in the pathogenesis of stroke and BBB breakdown has been unclear with contradictory experimental observations cited in the literature. For example, Nag et al., J. Neuropathology and Experimental Neurology 56:912 (1997), in their cortical cold-injury rat model, demonstrated the presence of mural VEGF in permeable pial vessels and arterioles within the damaged tissue and, from this observation, it was inferred that VEGF is one of several factors that may mediate BBB breakdown and edema formation. On the other hand, in Hayashi et al., J. Cerebral Blood Flow and Metabolism, 18:887 (1998), it is reported that VEGF itself, when applied topically on the surface of a reperfused rat brain after transient cerebral artery occlusion, reduced ischemic brain damage, infarct volume and edema formation.

SUMMARY OF THE INVENTION

The present invention provides antagonists of VEGF, including (a) antibodies and variants thereof which are capable of specifically binding to hVEGF, hVEGF receptor, or a complex comprising hVEGF in association with hVEGF receptor, (b) hVEGF receptor and variants thereof, and (c) hVEGF variants. The antagonists inhibit, sequester or neutralize the mitogenic, angiogenic, vascular permeability or other biological activity of hVEGF, and thus are useful for the treatment of diseases or conditions characterized by undesirable excessive neovascularization, including by way of example, tumors, and especially solid malignant tumors, rheumatoid arthritis, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation. The antagonists also are useful for the treatment of diseases or conditions such as edema which may be associated with, e.g., tumors, stroke, head trauma, ascites associated with malignancies, Meigs' syndrome, lung inflammation, nephrotic syndrome, pericardial effusion (such as that associated with pericarditis), and pleural effusion.

In other aspects, the VEGF antagonists are polyspecific monoclonal antibodies which are capable of binding to (a) a non-hVEGF epitope, for example, an epitope of a protein involved in thrombogenesis or thrombolysis, or a tumor cell surface antigen, or to (b) hVEGF, hVEGF receptor, or a complex comprising hVEGF in association with hVEGF receptor.

In still other aspects, the VEGF antagonists are conjugated with a cytotoxic moiety.

In another aspect, the invention concerns isolated nucleic acids encoding the monoclonal antibodies as hereinbefore described, and hybridoma cell lines which produce such monoclonal antibodies.

In another aspect, the invention concerns compositions, such as pharmaceutical compositions, comprising a VEGF antagonist in an amount effective in reducing or eliminating hVEGF-mediated mitogenic, angiogenic, or other biological activity in a mammal.

In a different aspect, the invention concerns methods of treatment comprising administering to a mammal, preferably a human patient in need of such treatment, an effective amount of a VEGF antagonist. If desired, the VEGF antagonist is co-administered, either simultaneously or sequentially, with one or more other VEGF antagonists, anti-tumor or anti-angiogenic substances, or therapies suitable for the disease or condition being treated.

In another aspect, the invention concerns a method for detecting hVEGF in a test sample by means of contacting the test sample with an antibody capable of binding specifically to hVEGF and determining the extent of such binding.

BRIEF DESCRIPTION OF THE DRAWINGS

FIGS. 1a-b shows the effect to anti-hVEGF monoclonal antibodies (A4.6.1 or B2.6.2) or an irrelevant anti-hepatocyte growth factor antibody (anti-HGF) on the binding of the anti-hVEGF monoclonal antibodies to hVEGF.

FIG. 2 shows the effect of anti-hVEGF monoclonal antibodies (A4.6.1 or B2.6.2) or an irrelevant anti-HGF antibody on the biological activity of hVEGF in cultures of bovine adrenal cortex capillary endothelial (ACE) cells.

FIGS. 3a-b shows the effect of anti-hVEGF monoclonal antibodies (A4.6.1, B2.6.2, or A2.6.1) on the binding of hVEGF to bovine ACE cells.

FIG. 4 shows the effect of A4.6.1 anti-hVEGF monoclonal antibody treatment on the rate of growth of growth of NEG55 tumors in mice.

FIG. 5 shows the effect of A4.6.1 anti-hVEGF monoclonal antibody treatment on the size of NEG55 tumors in mice after five weeks of treatment.

FIG. 6 shows the effect of A4.6.1 anti-hVEGF monoclonal antibody (VEGF Ab) treatment on the growth of SK-LMS-1 tumors in mice.

FIG. 7 shows the effect of varying doses of A4.6.1 anti-hVEGF monoclonal antibody (VEGF Ab) treatment on the growth of A673 tumors in mice.

FIG. 8 shows the effect of A4.6.1 anti-hVEGF monoclonal antibody on the growth and survival of NEG55 (G55) glioblastoma cells in culture.

FIG. 9 shows the effect of A4.6.1 anti-hVEGF monoclonal antibody on the growth and survival of A673 rhabdomyosarcoma cells in culture.

FIG. 10 shows the effect of A4.6.1 anti-hVEGF monoclonal antibody on human synovial fluid-induced chemotaxis of human endothelial cells.

FIG. 11 shows the effect of flt-IgG treatment on the extent of edematous tissue as depicted by high signal intensity on the T2-weighted MR image.

FIG. 12 shows representative T2-weighted MR images recorded 24 hours following onset of ischemia for both the control (top panel) and treatment group (bottom panel), showing reduction in edematous tissue in the treatment group.

FIG. 13 shows the effect of flt-IgG treatment on the size of infarction determined using high resolution anatomical MRI 8-12 weeks following onset of ischemia.

FIGS. 14A-B show an alignment of the amino acid sequences for the light and heavy variable domains respectively of affinity matured anti-VEGF antibodies compared to the F(ab)-12 antibody. CDRs are underlined and designated by L, light, or H, heavy chains, and numbers 1-3. The affinity matured sequences are designated YO243-1; YO238-3; YO313-1; and YO317. Differences from F(ab)-12 are shown in shaded boxes.

FIGS. 15A-B show an alignment of the amino acid sequences for the light and heavy variable domains respectively of affinity matured anti-VEGF antibodies compared to the F(ab)-12 antibody. CDRs are underlined and designated by L, light, or H, heavy chains, and numbers 1-3. The affinity matured sequences are designated YO192; YO238-3; YO239-19; and YO313-2. Differences from F(ab)-12 are shown in shaded boxes.

DETAILED DESCRIPTION OF THE INVENTION

The present invention provides antagonists of hVEGF which are capable of inhibiting, sequestering, or neutralizing one or more of the biological activities of hVEGF. Antagonists of hVEGF act by interfering with the binding of hVEGF to a cellular receptor, by incapacitating or killing cells which have been activated by hVEGF, or by interfering with vascular endothelial cell activation after hVEGF binding to a cellular receptor. All such points of intervention by an hVEGF antagonist shall be considered equivalent for purposes of this invention. Thus, included within the scope of the invention are antibodies, monoclonal antibodies and humanized antibodies, or fragments thereof, that bind to hVEGF, hVEGF receptor, or a complex comprising hVEGF in association with hVEGF receptor. Also included within the scope of the invention are fragments and amino acid sequence variants of hVEGF that bind to hVEGF receptor but which do not exhibit a biological activity of native hVEGF. Also included within the scope of the invention are hVEGF receptor and fragments and amino acid sequence variants thereof which are capable of binding hVEGF.

The term "hVEGF" as used herein refers to the 165-amino acid human vascular endothelial cell growth factor, and related 121-, 189-, and 206-amino acid vascular endothelial cell growth factors, as described by Leung, et al., Science 246:1306 (1989), and Houck, et al., Mol. Endocrin. 5:1806 (1991), together with the naturally occurring allelic and processed forms of those growth factors.

The term "hVEGF receptor" or "hVEGFr" as used herein refers to a cellular receptor for hVEGF, ordinarily a cell-surface receptor found on vascular endothelial cells, as well as fragments and variants thereof which retain the ability to bind hVEGF. Typically, the hVEGF receptors and fragments and variants thereof that are hVEGF antagonists will be in isolated form, rather than being integrated into a cell membrane or fixed to a cell surface as may be the case in nature. One example of a hVEGF receptor is the fms-like tyrosine kinase (flt or flt-1), a transmembrane receptor in the tyrosine kinase family. DeVries, et al., Science 255:989 (1992); Shibuya, et al., Oncogene 5:519 (1990). The full length flt receptor comprises an extracellular domain, a transmembrane domain, and an intracellular domain with tyrosine kinase activity. The extracellular domain is involved in the binding of hVEGF, whereas the intracellular domain is involved in signal transduction.

Another example of a hVEGF receptor is the flk-1 receptor (also referred to as KDR). Matthews, et al., Proc. Nat. Acad. Sci. 88:9026 (1991); Terman, et al., Oncogene 6:1677 (1991); Terman, et al., Biochem. Biophys. Res. Commun. 187:1579 (1992).

Binding of hVEGF to the flt receptor results in the formation of at least two high molecular weight complexes, having apparent molecular weight of 205,000 and 300,000 Daltons. The 300,000 Dalton complex is believed to be a dimer comprising two receptor molecules bound to a single molecule of hVEGF.

Variants of hVEGFr also are included within the scope hereof. Representative examples include truncated forms of a receptor in which at least the transmembrane and cytoplasmic domains are deleted from the full length receptor molecule, and fusions proteins in which non-hVEGFr polymers or polypeptides are conjugated to the hVEGFr or, preferably, truncated forms thereof. An example of such a non-hVEGF polypeptide is an immunoglobulin. In that case, for example, an extracellular domain sequence of the hVEGFr is substituted for the Fv domain of an immunoglobulin light or (preferably) heavy chain, with the C-terminus of the receptor extracellular domain covalently joined to the amino terminus of the CH1, hinge, CH2 or other fragment of the heavy chain. Such variants are made in the same fashion as known immunoadhesins. See e.g., Gascoigne, et al., Proc. Nat. Acad. Sci. 84:2936 (1987); Capon, et al., Nature 337:525 (1989); Aruffo, et al., Cell 61:1303 (1990); Ashkenazi, et al., Proc. Nat. Acad. Sci. 88:10535 (1991); Bennett, et al., J. Biol. Chem. 266:23060 (1991). Examples of various flt-IgG fusion proteins are described in Example 3 below. Truncated forms of the extracellular domain of the hVEGF receptor contemplated for use in the invention include ECD fragments (for instance, having one or more amino acids in the ECD sequence deleted) and ECD forms having one or more immunoglobulin-like domains in the ECD deleted. Example 3B describes, for instance, a truncated ECD form which includes only the first three immunoglobulin-like domains of flt fused to a Fc-IgG. Preferably, a truncated form of the ECD used in making an antagonist molecule will include sufficient immunoglobulin-like domain(s) to ensure a desired binding to hVEGF.

In other embodiments, the hVEGFr or fragments or variants thereof are conjugated to a non-proteinaceous polymer such as polyethylene glycol (PEG) (see e.g., Davis, et al., U.S. Pat. No. 4,179,337; Goodson, et al., BioTechnology 8:343-346 (1990); Abuchowski, et al., J. Biol. Chem. 252:3578 (1977); Abuchowski, et al., J. Biol. Chem. 252:3582 (1977)) or carbohydrates (see e.g., Marshall, et al., Arch. Biochem. Biophys., 167:77 (1975)). This can serve to extend the biological half-life of the hVEGFr and reduce the possibility that the receptor will be immunogenic in the mammal to which it is administered.

The hVEGFr is used in substantially the same fashion as antibodies to hVEGF, taking into account the affinity of the antagonist and its valency for hVEGF. An extracellular domain sequence of hVEGF receptor, either by itself or fused to an immunoglobulin polypeptide or other carrier polypeptide, is especially useful as an antagonist of hVEGF, by virtue of its ability to sequester hVEGF that is present in a host but that is not bound to hVEGFr on a cell surface.

HVEGFr and fragments and variants thereof also are useful in screening assays to identify agonists and antagonists of hVEGF. For example, host cells transfected with DNA encoding hVEGFr (for example, flt or flk-1) overexpress the receptor polypeptide on the cell surface, making such recombinant host cells ideally suited for analyzing the ability of a test compound (for example, a small molecule, linear or cyclic peptide, or polypeptide) to bind to hVEGFr. hVEGFr and hVEGFr fusion proteins, such as an hVEGFr-IgG fusion protein, may be used in a similar fashion. For example, the fusion protein is bound to an immobilized support and the ability of a test compound to displace radiolabeled hVEGF from the hVEGFr domain of the fusion protein is determined.

The term "recombinant" used in reference to hVEGF, hVEGF receptor, antibodies, or other proteins, refers to proteins that are produced by recombinant DNA expression in a host cell. The host cell may be prokaryotic (for example, a bacterial cell such as *E. coli*) or eukaryotic (for example, a yeast or a mammalian cell).

Antagonist Antibodies

The term "monoclonal antibody" as used herein refers to an antibody obtained from a population of substantially homogeneous antibodies, i.e., the individual antibodies comprising the population are identical in specificity and affinity except for possible naturally occurring mutations that may be present in minor amounts. It should be appreciated that as a result of such naturally occurring mutations and the like, a monoclonal antibody composition of the invention, which will predominantly contain antibodies capable of specifically binding hVEGF, hVEGFr, or a complex comprising hVEGF in association with hVEGFr ("hVEGF-hVEGFr complex"), may also contain minor amounts of other antibodies.

Thus, the modifier "monoclonal" indicates the character of the antibody as being obtained from such a substantially homogeneous population of antibodies, and is not to be construed as requiring production of the antibody by any particular method. For example, monoclonal antibodies of the invention may be made using the hybridoma method first described by Kohler & Milstein, Nature 256:495 (1975), or may be made by recombinant DNA methods. See, e.g., Cabilly, et al., U.S. Pat. No. 4,816,567.

In the hybridoma method, a mouse or other appropriate host animal is immunized with antigen by subcutaneous, intraperitoneal, or intramuscular routes to elicit lymphocytes that produce or are capable of producing antibodies that will specifically bind to the protein(s) used for immunization. Alternatively, lymphocytes may be immunized in vitro. Lymphocytes then are fused with myeloma cells using a suitable fusing agent, such as polyethylene glycol, to form a hybridoma cell. Goding, *Monoclonal Antibodies: Principles and Practice*, pp. 59-103 (Academic Press, 1986).

The antigen may be hVEGF, hVEGFr, or hVEGF-hVEGFr complex. The antigen optionally is a fragment or portion or variant of any one of hVEGF or hVEGFr having one or more amino acid residues that participate in the binding of hVEGF to one of its receptors. For example, immunization with an extracellular domain sequence of an hVEGFr (such as, a truncated hVEGFr polypeptide lacking at least transmembrane and intracellular domains) will be especially useful in producing antibodies that are antagonists of hVEGF, since it is region(s) within the extracellular domain that are involved in hVEGF binding.

Monoclonal antibodies capable of binding hVEGF-hVEGFr complex are useful, particularly if they do not also bind to non-associated (non-complexed) hVEGF and hVEGFr. Such antibodies thus only bind to cells undergoing immediate activation by hVEGF and accordingly are not sequestered by free hVEGF or hVEGFr as is normally found in a mammal. Such antibodies typically bind an epitope that spans one or more points of contact between the receptor and hVEGF. Such antibodies have been produced for other ligand receptor complexes and may be produced here in the same fashion. These antibodies need not, and may not, neutralize or inhibit a biological activity of non-associated hVEGF or hVEGFr, whether or not the antibodies are capable of binding to non-associated hVEGF or hVEGFr.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, SP-2 cells available from the American Type Culture Collection, Manassas, Va. USA, and P3X63Ag8U.1 cells described by Yelton, et al., Curr. Top. Microbiol. Immunol. 81:1 (1978). Human myeloma and mouse-human heteromyeloma cell lines also have been described for the production of human monoclonal antibodies. Kozbor, J. Immunol. 133:3001 (1984); Brodeur, et al., *Monoclonal Antibody Production Techniques and Applications*, pp. 51-63 (Marcel Dekker, Inc., New York, 1987).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The monoclonal antibodies of the invention are those that preferentially immunoprecipitate hVEGF, hVEGFr, or hVEGF-hVEGFr complex, or that preferentially bind to at least one of those antigens in a binding assay, and that are capable of inhibiting a biological activity of hVEGF.

After hybridoma cells are identified that produce antagonist antibodies of the desired specificity, affinity, and activity, the clones may be subcloned by limiting dilution procedures and grown by standard methods. Goding, *Monoclonal Antibodies: Principles and Practice*, pp. 59-104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese Hamster ovary (CHO) cells, or myeloma cells that do not otherwise produce immunoglobulin protein, to obtain the synthesis of monoclonal antibodies in the recombinant host cells.

The DNA optionally may be modified in order to change the character of the immunoglobulin produced by its expression. For example, humanized forms of murine antibodies are produced by substituting a complementarity determining region (CDR) of the murine antibody variable domain for the corresponding region of a human antibody. In some embodiments, selected framework region (FR) amino acid residues of the murine antibody also are substituted for the corresponding amino acid residues in the human antibody. Carter, et al., Proc. Nat. Acad. Sci. 89:4285 (1992); Carter, et al., BioTechnology 10:163 (1992). Chimeric forms of murine antibodies also are produced by substituting the coding sequence for selected human heavy and light constant chain domains in place of the homologous murine sequences. Cabilly, et al., U.S. Pat. No. 4,816,567; Morrison, et al., Proc. Nat. Acad. Sci. 81:6851 (1984).

Particular humanized antibodies contemplated for use in the present invention include the humanized and affinity matured anti-hVEGF antibodies described in published PCT applications WO 98/54331 (published Oct. 15, 1998) and WO 98/54332 (published Oct. 15, 1998). Such humanized or affinity matured anti-VEGF antibodies may be prepared or made using the methods and techniques described in WO 98/54331 and WO 98/54332. Preferably, the anti-hVEGF antibody comprises the humanized F(ab), designated as F(ab)-12, or the affinity matured antibody, designated as YO317, in the above referenced PCT applications. FIGS. 14A-B and 15A-B illustrate the amino acid sequences (light and heavy chains) for these anti-VEGF antibodies, along with other affinity matured anti-VEGF antibodies, designated as YO192; YO238-3; YO239-19; YO313-2; YO243-1; and YO313-1. All such anti-VEGF antibodies are contemplated for use in the methods described herein. As disclosed in these published PCT applications, several of the humanized and affinity matured antibodies were demonstrated to reduce or inhibit VEGF activity in different types of in vitro assays, and thus act as VEGF antagonists.

The antibodies included within the scope of the invention thus include variant antibodies, such as chimeric (including "humanized") antibodies and hybrid antibodies comprising immunoglobulin chains capable of binding hVEGF, hVEGFr, or hVEGF-hVEGFr complex, and a non-hVEGF epitope.

The antibodies herein include all species of origin, and immunoglobulin classes (e.g., IgA, IgD, IgE, IgG, and IgM) and subclasses, as well as antibody fragments (e.g., Fab, F(ab')$_2$, and Fv), so long as they are capable of binding hVEGF, hVEGFr, or hVEGF-hVEGFr complex, and are capable of antagonizing a biological activity of hVEGF.

In a preferred embodiment of the invention, the antibody will have an affinity for the immunizing antigen of at least about $10^9$ liters/mole, as determined, for example, by the Scatchard analysis of Munson & Pollard, Anal. Biochem. 107:220 (1980). Also, the monoclonal antibody typically will inhibit the mitogenic or angiogenic activity of hVEGF at least about 50%, preferably greater than 80%, and most preferably greater than 90%, as determined, for example, by an in vitro cell survival or proliferation assay, such as described in Example 2 or as described in WO 98/54331 and WO 98/54332.

For some therapeutic and diagnostic applications, it is desirable that the monoclonal antibody be reactive with fewer than all of the different molecular forms of hVEGF. For example, it may be desirable to have a monoclonal antibody that is capable of specifically binding to the 165-amino acid sequence hVEGF but not to the 121- or 189-amino acid sequence hVEGF polypeptides. Such antibodies are readily identified by comparative ELISA assays or comparative immunoprecipitation of the different hVEGF polypeptides.

Conjugates with Cytotoxic Moieties

In some embodiments it is desirable to provide a cytotoxic moiety conjugated to a hVEGF-specific monoclonal antibody or to hVEGFr. In these embodiments the cytotoxin serves to incapacitate or kill cells which are expressing or binding hVEGF or its receptor. The conjugate is targeted to the cell by the domain which is capable of binding to hVEGF, hVEGFr, or hVEGF-hVEGFr complex. Thus, monoclonal antibodies that are capable of binding hVEGF, hVEGFr, or hVEGF-hVEGFr complex are conjugated to cytotoxins. Similarly, hVEGFr is conjugated to a cytotoxin. While the monoclonal antibodies optimally are capable of neutralizing the activity of hVEGF alone (without the cytotoxin), it is not necessary in this embodiment that the monoclonal antibody or receptor be capable of any more than binding to hVEGF, hVEGFr, or hVEGF-hVEGFr complex.

Typically, the cytotoxin is a protein cytotoxin, e.g. diptheria, ricin or *Pseudomonas* toxin, although in the case of certain classes of immunoglobulins the Fc domain of the monoclonal antibody itself may serve to provide the cytotoxin (e.g., in the case of IgG2 antibodies, which are capable of fixing complement and participating in antibody-dependent cellular cytotoxicity (ADCC)). However, the cytotoxin does not need to be proteinaceous and may include chemotherapeutic agents heretofore employed, for example, for the treatment of tumors.

The cytotoxin typically is linked to a monoclonal antibody or fragment thereof by a backbone amide bond within (or in place of part or all of) the Fc domain of the antibody. Where the targeting function is supplied by hVEGFr, the cytotoxic moiety is substituted onto any domain of the receptor that does not participate in hVEGF binding; preferably, the moiety is substituted in place of or onto the transmembrane and or cytoplasmic domains of the receptor. The optimal site of substitution will be determined by routine experimentation and is well within the ordinary skill.

Conjugates which are protein fusions are easily made in recombinant cell culture by expressing a gene encoding the conjugate. Alternatively, the conjugates are made by covalently crosslinking the cytotoxic moiety to an amino acid residue side chain or C-terminal carboxyl of the antibody or the receptor, using methods known per se such as disulfide exchange or linkage through a thioester bond using for example iminothiolate and methyl-4-mercaptobutyrimadate.

Conjugates with Other Moieties

The monoclonal antibodies and hVEGFr that are antagonists of hVEGF also can also be conjugated to substances that may not be readily classified as cytotoxins in their own right, but which augment the activity of the compositions herein. For example, monoclonal antibodies or hVEGFr capable of binding to hVEGF, hVEGFr, or hVEGF-hVEGFr complex are fused with heterologous polypeptides, such as viral sequences, with cellular receptors, with cytokines such as TNF, interferons, or interleukins, with polypeptides having procoagulant activity, and with other biologically or immunologically active polypeptides. Such fusions are readily made by recombinant methods. Typically such non-immunoglobulin polypeptides are substituted for the constant domain(s) of an anti-hVEGF or anti-hVEGF-hVEGFr complex antibody, or for the transmembrane and/or intracellular domain of an hVEGFr. Alternatively, they are substituted for a variable domain of one antigen binding site of an anti-hVEGF antibody described herein.

In preferred embodiments, such non-immunoglobulin polypeptides are joined to or substituted for the constant domains of an antibody described herein. Bennett, et al., J. Biol. Chem. 266:23060-23067 (1991). Alternatively, they are substituted for the Fv of an antibody herein to create a chimeric polyvalent antibody comprising at least one remaining antigen binding site having specificity for hVEGF, hVEGFr, or a hVEGF-hVEGFr complex, and a surrogate antigen binding site having a function or specificity distinct from that of the starting antibody.

Heterospecific Antibodies

Monoclonal antibodies capable of binding to hVEGF, hVEGFr, or hVEGF-hVEGFr complex need only contain a single binding site for the enumerated epitopes, typically a single heavy-light chain complex or fragment thereof. However, such antibodies optionally also bear antigen binding domains that are capable of binding an epitope not found within any one of hVEGF, hVEGFr, or hVEGF-hVEGFr complex. For example, substituting the corresponding amino acid sequence or amino acid residues of a native anti-hVEGF, anti-HVEGFr, or anti-hVEGF-hVEGFr complex antibody with the complementarity-determining and, if necessary, framework residues of an antibody having specificity for an antigen other than hVEGF, hVEGFr, or hVEGF-hVEGFr complex will create a polyspecific antibody comprising one antigen binding site having specificity for hVEGF, hVEGFr, or hVEGF-hVEGFr complex, and another antigen binding site having specificity for the non-hVEGF, hVEGFr, or hVEGF-hVEGFr complex antigen. These antibodies are at least bivalent, but may be polyvalent, depending upon the number of antigen binding sites possessed by the antibody class chosen. For example, antibodies of the IgM class will be polyvalent.

In preferred embodiments of the invention such antibodies are capable of binding an hVEGF or hVEGFr epitope and either (a) a polypeptide active in blood coagulation, such as protein C or tissue factor, (b) a cytotoxic protein such as tumor necrosis factor (TNF), or (c) a non-hVEGFr cell surface receptor, such as CD4, or HER-2 receptor (Maddon, et al., Cell 42:93 (1985); Coussens, et al., Science 230:1137 (1985)). Heterospecific, multivalent antibodies are conveniently made by cotransforming a host cell with DNA encoding the heavy and light chains of both antibodies and thereafter recovering, by immunoaffinity chromatography or the like, the proportion of expressed antibodies having the desired antigen binding properties. Alternatively, such antibodies are made by in vitro recombination of monospecific antibodies.

Monovalent Antibodies

Monovalent antibodies capable of binding to hVEGFr or hVEGF-hVEGFr complex are especially useful as antagonists of hVEGF. Without limiting the invention to any particular mechanism of biological activity, it is believed that activation of cellular hVEGF receptors proceeds by a mechanism wherein the binding of hVEGF to cellular hVEGF receptors induces aggregation of the receptors, and in turn activates intracellular receptor kinase activity. Because monovalent anti-hVEGF receptor antibodies cannot induce such aggregation, and therefore cannot activate hVEGF receptor by that mechanism, they are ideal antagonists of hVEGF.

It should be noted, however, that these antibodies should be directed against the hVEGF binding site of the receptor or should otherwise be capable of interfering with hVEGF binding to the receptor hVEGF, such as by sterically hindering hVEGF access to the receptor. As described elsewhere herein, however, anti-hVEGFr antibodies that are not capable of interfering with hVEGF binding are useful when conjugated to non-immunoglobulin moieties, for example, cytotoxins.

Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. For example, Fab fragments are prepared by enzymatic cleavage of intact antibody.

Diagnostic Uses

For diagnostic applications, the antibodies or hVEGFr of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody or hVEGFr to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). The antibodies and receptors of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard (which may be hVEGF or an immunologically reactive portion thereof) to compete with the test sample analyte (hVEGF) for binding with a limited amount of antibody. The amount of hVEGF in the test sample is inversely proportional to the amount of standard that becomes bound to the antibodies or receptors. To facilitate determining the amount of standard that becomes bound, the antibodies or receptors generally are insolubilized before or after the competition, so that the standard and analyte that are bound to the antibodies or receptors may conveniently be separated from the standard and analyte which remain unbound.

Sandwich assays involve the use of two antibodies or receptors, each capable of binding to a different immunogenic portion, or epitope, of the protein to be detected. In a sandwich assay, the test sample analyte is bound by a first antibody or receptor which is immobilized on a solid support, and thereafter a second antibody binds to the analyte, thus forming an insoluble three part complex. David & Greene, U.S. Pat. No. 4,376,110. The second antibody or receptor may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies or receptor herein also is useful for in vivo imaging, wherein an antibody or hVEGFr labeled with a detectable moiety is administered to a patient, preferably into the bloodstream, and the presence and location of the labeled antibody or receptor in the patient is assayed. This imaging technique is useful, for example, in the staging and treatment of neoplasms. The antibody or hVEGFr is labeled with any moiety that is detectable in a mammal, whether by nuclear magnetic resonance, radiology, or other detection means known in the art.

Antagonist Variants of hVEGF

In addition to the antibodies described herein, other useful antagonists of hVEGF include fragments and amino acid sequence variants of native hVEGF that bind to hVEGF receptor but that do not exhibit the biological activity of native hVEGF. For example, such antagonists include fragments and amino acid sequence variants that comprise a receptor binding domain of hVEGF, but that lack a domain conferring biological activity, or that otherwise are defective in activating cellular hVEGF receptors, such as in the case of a fragment or an amino acid sequence variant that is deficient in its ability to induce aggregation or activation of cellular hVEGF receptors. The term "receptor binding domain" refers to the amino acid sequences in hVEGF that are involved in hVEGF receptor binding. The term "biological activity domain" or "domain conferring biological activity" refers to an amino acid sequence in hVEGF that confer a particular biological activity of the factor, such as mitogenic, angiogenic, or vascular permeability activity.

The observation that hVEGF appears to be capable of forming a complex with two or more hVEGFr molecules on the surface of a cell suggests that hVEGF has at least two discrete sites for binding to hVEGFr and that it binds to such cellular receptors in sequential fashion, first at one site and then at the other before activation occurs, in the fashion of growth hormone, prolactin and the like (see e.g., Cunningham, et al., Science 254:821 (1991); deVos, et al., Science 255:306 (1992); Fuh, et al., Science 256:1677 (1992)). Accordingly, antagonist variants of hVEGF are selected in which one receptor binding site of hVEGF (typically the site involved in the initial binding of hVEGF to hVEGFr) remains unmodified (or if modified is varied to enhance binding), while a second receptor binding site of hVEGF typically is modified by nonconservative amino acid residue substitution(s) or deletion(s) in order to render that binding site inoperative.

Receptor binding domains in hVEGF and hVEGF binding domains in hVEGFr are determined by methods known in the art, including X-ray studies, mutational analyses, and antibody binding studies. The mutational approaches include the techniques of random saturation mutagenesis coupled with selection of escape mutants, and insertional mutagenesis. Another strategy suitable for identifying receptor-binding domains in ligands is known as alanine (Ala)-scanning mutagenesis. Cunningham, et al., Science 244, 1081-1985 (1989). This method involves the identification of regions that contain charged amino acid side chains. The charged residues in each region identified (i.e. Arg, Asp, His, Lys, and Glu) are replaced (one region per mutant molecule) with Ala and the receptor binding of the obtained ligands is tested, to assess the importance of the particular region in receptor binding. A further powerful method for the localization of receptor binding domains is through the use of neutralizing anti-hVEGF antibodies. Kim, et al., Growth Factors 7:53 (1992). Usually a combination of these and similar methods is used for localizing the domains involved in receptor binding.

The term "amino acid sequence variant" used in reference to hVEGF refers to polypeptides having amino acid sequences that differ to some extent from the amino acid sequences of the native forms of hVEGF. Ordinarily, antagonist amino acid sequence variants will possess at least about 70% homology with at least one receptor binding domain of a native hVEGF, and preferably, they will be at least about 80%, more preferably at least about 90% homologous with a receptor binding domain of a native hVEGF. The amino acid sequence variants possess substitutions, deletions, and/or insertions at certain positions within the amino acid sequence of native hVEGF, such that the variants retain the ability to bind to hVEGF receptor (and thus compete with native hVEGF for binding to hVEGF receptor) but fail to induce one or more of the biological effects of hVEGF, such as endothelial cell proliferation, angiogenesis, or vascular permeability.

"Homology" is defined as the percentage of residues in the amino acid sequence variant that are identical with the residues in the amino acid sequence of a receptor binding domain of a native hVEGF after aligning the sequences and introducing gaps, if necessary, to achieve the maximum percent homology and not considering any conservative substitutions as part of the percentage of amino acid homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991. Those skilled in the art can determine, using routine skill, appropriate parameters for measuring alignment, including any algorithms needed to achieve maximal alignment over the length of the sequences being compared.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acid residues in a native sequence removed. Ordinarily, deletional variants will have one or two amino acid residues deleted in a particular region of the molecule.

Fragments and amino acid sequence variants of hVEGF are readily prepared by methods known in the art, such as by site directed mutagenesis of the DNA encoding the native factor. The mutated DNA is inserted into an appropriate expression vector, and host cells are then transfected with the recombinant vector. The recombinant host cells and grown in suitable culture medium, and the desired fragment or amino acid sequence variant expressed in the host cells then is recovered from the recombinant cell culture by chromatographic or other purification methods.

Alternatively, fragments and amino acid variants of hVEGF are prepared in vitro, for example by proteolysis of native hVEGF, or by synthesis using standard solid-phase peptide synthesis procedures as described by Merrifield (J. Am. Chem. Soc. 85:2149 (1963)), although other equivalent chemical syntheses known in the art may be used. Solid-phase synthesis is initiated from the C-terminus of the peptide by coupling a protected α-amino acid to a suitable resin. The amino acids are coupled to the peptide chain using techniques well known in the art for the formation of peptide bonds.

Therapeutic Uses

The terms "treating", "treatment", "therapy" and "therapeutic" as used herein refer to curative therapy, prophylactic therapy and preventative therapy.

For therapeutic applications, the antagonists of the invention are administered to a mammal, preferably a human, in an acceptable dosage form, including those that may be administered to a human intravenously as a bolus or by continuous infusion over a period of time, by intramuscular, intraperitoneal, intra-cerebrospinal, subcutaneous, intra-articular, intrasynovial, intradural, intrathecal, oral, topical, or inhalation routes. The antagonists also are suitably administered by intratumoral, peritumoral, intralesional, or perilesional routes, to exert local as well as systemic therapeutic effects. The intraperitoneal route is expected to be particularly useful, for example, in the treatment of ovarian tumors. Intravenous infusion is expected to be particularly useful for instance, in the treatment of cerebral edema.

Such dosage forms encompass carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antagonist include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms can be suitably used. Such forms include, for example, microcapsules, nano-capsules, liposomes, plasters, inhalation forms, nose sprays, sublingual tablets, and sustained-release preparations. The antagonist will typically be formulated in such vehicles at a concentration of about 0.1 mg/ml to 100 mg/ml.

Suitable examples of sustained release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate) as described by Langer et al., J. Biomed. Mater. Res. 15:167 (1981) and Langer, Chem. Tech., 12: 98-105 (1982), or poly (vinylalcohol), polylactides (U.S. Pat. No. 3,773,919), copolymers of L-glutamic acid and gamma ethyl-L-glutamate (Sidman et al., Biopolymers, 22:547 (1983), non-degradable ethylene-vinyl acetate (Langer et al., supra), degradable lactic acid-glycolic acid copolymers such as the Lupron Depot™ (injectable micropheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptide antagonists remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release hVEGF antagonist compositions also include liposomally entrapped antagonist antibodies or hVEGFr. Liposomes containing the antagonists are prepared by methods known in the art, such as described in Epstein, et al., Proc. Natl. Acad. Sci. USA, 82:3688 (1985); Hwang, et al., Proc. Natl. Acad. Sci. USA, 77:4030 (1980); U.S. Pat. No. 4,485,045; U.S. Pat. No. 4,544,545. Ordinarily the liposomes are the small (about 200-800 Angstroms) unilamelar type in which the lipid content is greater than about 30 mol. % cholesterol, the selected proportion being adjusted for the optimal HRG therapy. Liposomes with enhanced circulation time are disclosed in U.S. Pat. No. 5,013,556.

Another use of the present invention comprises incorporating an hVEGF antagonist into formed articles. Such articles can be used, for instance, in modulating endothelial cell growth and angiogenesis. In addition, tumor invasion and metastasis may be modulated with these articles.

An appropriate and effective dosage of antagonist will depend on the type of disease or condition to be treated, as defined herein, the severity and course of the disease or condition, whether the antagonists are administered for preventive or therapeutic purposes, previous therapy, the patient's clinical history and response to the antagonist, and the discretion of the attending physician. An effective dosage of antagonist will typically be that amount of antagonist administered to achieve the maximal of desired amount of inhibition of VEGF biological activity. The antagonist is suitably administered to the patient at one time or over a series of treatments.

The hVEGF antagonists are useful in the treatment of various neoplastic and non-neoplastic diseases and conditions. Neoplasms and related conditions that are amenable to treatment include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, and Meigs' syndrome.

In one embodiment, vascularization of tumors is attacked in combination therapy. One or more hVEGF antagonists are administered to tumor-bearing patients at therapeutically effective doses as determined for example by observing necrosis of the tumor or its metastatic foci, if any. This therapy is continued until such time as no further beneficial effect is observed or clinical examination shows no trace of the tumor or any metastatic foci. Other auxiliary agents such as tumor necrosis factor (TNF), alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see Esmon, et al., PCT Patent Publication No. WO 91/01753, published 21 Feb. 1991), or heat or radiation.

Since the auxiliary agents will vary in their effectiveness it is desirable to compare their impact on the tumor by matrix screening in conventional fashion. The administration of hVEGF antagonist and, for instance, TNF, can be repeated until the desired clinical effect is achieved. Alternatively, the hVEGF antagonist(s) can be administered together with TNF and, optionally, auxiliary agent(s). In instances where solid tumors are found in the limbs or in other locations susceptible to isolation from the general circulation, the therapeutic agents described herein are administered to the isolated tumor or organ. In other embodiments, a FGF or platelet-derived growth factor (PDGF) antagonist, such as an anti-FGF or an anti-PDGF neutralizing antibody, is administered to the patient in conjunction with the hVEGF antagonist. Treatment with hVEGF antagonists optimally may be suspended during periods of wound healing or desirable neovascularization.

Non-neoplastic conditions that are amenable to treatment include rheumatoid arthritis, psoriasis, atherosclerosis, diabetic and other retinopathies, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

Age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VEGF antagonists of the present invention are expected to be especially useful in reducing the severity of AMD.

Other conditions that are amendable to treatment include edema. Herein, the term "edema" is used in a general sense and includes conditions in the body or accompanying stroke or head injury characterized by an increase in the extravascular tissue water content, either due to increased free extracellular water alone, or in combination with increased intracellular water. The edema may be present in various tissues in the body. In particular, it is contemplated that the hVEGF antagonists may be employed to treat central nervous system (CNS) edema, including cerebral edema, typically characterized by an increase in brain volume, as well as spinal cord or spinal canal edema or other conditions leading to increased intracranial pressure (such as local spinal cord injury). Increase in brain volume can be, for instance, the result of increased cerebral blood volume and/or increased tissue water content. The term "edema" used herein includes the pathological conditions referred to in the art as vasogenic edema and cytotoxic edema. Typically, the condition referred to as vasogenic edema has been characterized as being associated with the disruption of the blood-brain barrier (BBB) while cytotoxic edema has been characterized as being associated with an intact BBB. Cerebral edema is described generally in the review article, Hariri, Neurosurgical Intensive Care 5:687 (1994).

Edema in a mammal may result from or accompany a variety of pathological conditions or stimuli, including but not limited to, acute hypertension, meningitis, encephalitis, abscess, neoplastic diseases (such as described above) (particularly solid tumors), trauma (such as head injury), hemorrhage, viral infection, cerebral malaria, stroke, radiation, multiple sclerosis, post cardiac arrest, birth asphyxia, glutamate toxicity, encephalopathy, hypoxia, ischemia and renal dialysis.

In particular, the invention contemplates therapy using the hVEGF antagonists to treat cerebral edema, including cerebral edema accompanying neoplasm(s) in the brain and cerebral edema accompanying stroke. In mammals having a neoplasm(s) in brain tissue, it is common for the mammal to develop or experience cerebral edema. It is contemplated that the hVEGF antagonists of the present invention can be administered, alone or in combination with other therapies, like chemotherapy or radiation therapy administered to treat the brain neoplasm, to reduce or inhibit such edema in the brain.

It is also common for mammals having or having undergone stroke to develop or experience cerebral edema. The term stroke in the present application is used in a general sense and includes the clinical conditions known to the skilled practitioner as ischemic stroke and hemorrhagic stroke. It is recognized within the art that stroke in a patient may be characterized or classified as various particular types of stroke, depending for instance, upon the etiology or pathology of the interruption of blood flow, the types of cells or tissues affected, and the presence of blood extravasation into tissue (such as brain tissue). The different types of stroke that have been clinically characterized include but are not limited to, thrombotic stroke, embolic stroke, hemodynamic stroke, lacunar stroke, and hemorrhagic strokes derived or resulting from intracerebral, subarachnoid, intraventricular, or subdural hemorrhage. The skilled medical practitioner will readily appreciate and understand the nature of such stroke conditions, and be able to detect and diagnosis the presence or symptoms of such conditions in patients. The present inventive methods contemplate that the hVEGF antagonist molecules can be used in the treatment of all such stroke conditions, particularly to reduce or inhibit edema and protect against cell and tissue damage. The hVEGF antagonists can be administered as an acute treatment following stroke onset to reduce or inhibit for instance, cerebral edema, thereby enhancing the mammalls recovery from the stroke. The use of the hVEGF antagonists are beneficial in that the treatment may prevent or avoid having to perform surgery (like a craniotomy) on the mammal to reduce or alleviate intracranial pressure due to excess water accumulation in brain tissues. It is also contemplated that upon reduction or prevention of such edema by the hVEGF antagonists, there will be a reduction (i.e., protective effect) in the amount of brain and neuronal tissue that can typically be damaged by intracranial pressure and edema.

Depending on the type and severity of the disease or condition being treated, about 1 μg/kg to 15 mg/kg of antagonist is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is repeated until a desired suppression of disease symptoms occurs. However, other dosage regimens may be useful. For instance, in the methods of treating cerebral edema or stroke, it may be desirable to administer the hVEGF antagonist(s) immediately upon detection or diagnosis in the patient, within several hours of injury or onset of stroke, or within 1 to 4 days thereafter. The desired administration protocol will typically be within the discretion of the medical practitioner. The progress of the hVEGF antagonist therapy is easily monitored by conventional techniques and assays, including, for example, radiographic techniques (in particular, magnetic resonance imaging, MRI) for neoplastic conditions and edema formation associated with trauma or stroke, or monitoring intracranial pressure for cerebral edema.

According to another embodiment of the invention, the effectiveness of the antagonist in preventing or treating a condition or disease may be improved by administering the antagonist serially or in combination with another agent that is effective for those purposes, such as tumor necrosis factor (TNF), an antibody capable of inhibiting or neutralizing the angiogenic activity of acidic or basic fibroblast growth factor (FGF) or hepatocyte growth factor (HGF), an antibody capable of inhibiting or neutralizing the coagulant activities of tissue factor, protein C, or protein S (see Esmon, et al., PCT Patent Publication No. WO 91/01753, published 21 Feb. 1991), an antibody capable of binding to HER2 receptor (see Hudziak, et al., PCT Patent Publication No. WO 89/06692, published 27 Jul. 1989), or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Particularly in the treatment of edema or stroke, the antagonist may be administered serially or in combination with agents such as antiviral, antifungal or antiparasitic agents, antibiotics, thrombolytic agents (such as t-PA), osmotic therapy agents (e.g., mannitol), or steroids (like Decadron or prednisone). Use of such agents in combination with the antagonist will be within the ordinary skill of the medical practitioner, and of course, selection of such agents would depend, for instance, on the disease or condition being treated.

In a further method of treatment provided in the present application, it is contemplated that the hVEGF antagonist may be administered serially with hVEGF, particularly in the treatment of stroke. Upon diagnosis or detection of stroke, the hVEGF antagonist may be administered immediately or within approximately 1 to 4 days after onset of the stroke. It is believed that following completion of the administration of the antagonist to reduce or inhibit edema formation, it may be beneficial to administer to the patient an amount of hVEGF sufficient to stimulate or promote re-vascularization. Preferably, the hVEGF would be a recombinant form of hVEGF and would be administered in a pharmaceutically-acceptable carrier.

Other Uses

The anti-hVEGF antibodies of the invention also are useful as affinity purification agents. In this process, the antibodies against hVEGF are immobilized on a suitable support, such a Sephadex resin or filter paper, using methods well known in the art. The immobilized antibody then is contacted with a sample containing the hVEGF to be purified, and thereafter the support is washed with a suitable solvent that will remove substantially all the material in the sample except the hVEGF, which is bound to the immobilized antibody. Finally, the support is washed with another suitable solvent, such as glycine buffer, pH 5.0, that will release the hVEGF from the antibody.

The following examples are offered by way of illustration only and are not intended to limit the invention in any manner. All patent and literature citations in the specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Preparation of Anti-Hvegf Monoclonal Antibodies

To obtain hVEGF conjugated to keyhole limpet hemocyanin (KLH) for immunization, recombinant hVEGF (165 amino acids), Leung, et al., Science 246:1306 (1989), was mixed with KLH at a 4:1 ratio in the presence of 0.05% glutaraldehyde and the mixture was incubated at room temperature for 3 hours with gentle stirring. The mixture then was dialyzed against phosphate buffered saline (PBS) at 4° C. overnight.

Balb/c mice were immunized four times every two weeks by intraperitoneal injections with 5 µg of hVEGF conjugated to 20 µg of KLH, and were boosted with the same dose of hVEGF conjugated to KLH four days prior to cell fusion.

Spleen cells from the immunized mice were fused with P3X63Ag8U.1 myeloma cells, Yelton, et al., Curr. Top. Microbiol. Immunol. 81:1 (1978), using 35% polyethylene glycol (PEG) as described. Yarmush, et al., Proc. Nat. Acad. Sci. 77:2899 (1980). Hybridomas were selected in HAT medium.

Supernatants from hybridoma cell cultures were screened for anti-hVEGF antibody production by an ELISA assay using hVEGF-coated microtiter plates. Antibody that was bound to hVEGF in each of the wells was determined using alkaline phosphatase-conjugated goat anti-mouse IgG immunoglobulin and the chromogenic substrate p-nitrophenyl phosphate. Harlow & Lane, *Antibodies: A Laboratory Manual*, p. 597 (Cold Spring Harbor Laboratory, 1988). Hybridoma cells thus determined to produce anti-hVEGF antibodies were subcloned by limiting dilution, and two of those clones, designated A4.6.1 and B2.6.2, were chosen for further studies.

Example 2

Characterization of Anti-Hvegf Monoclonal Antibodies

A. Antigen Specificity

The binding specificities of the anti-hVEGF monoclonal antibodies produced by the A4.6.1 and B2.6.2 hybridomas were determined by ELISA. The monoclonal antibodies were added to the wells of microtiter plates that previously had been coated with hVEGF, FGF, HGF, or epidermal growth factor (EGF). Bound antibody was detected with peroxidase conjugated goat anti-mouse IgG immunoglobulins. The results of those assays confirmed that the monoclonal antibodies produced by the A4.6.1 and B2.6.2 hybridomas bind to hVEGF, but not detectably to those other protein growth factors.

B. Epitope Mapping

A competitive binding ELISA was used to determine whether the monoclonal antibodies produced by the A4.6.1 and B2.6.2 hybridomas bind to the same or different epitopes (sites) within hVEGF. Kim, et al., Infect. Immun. 57:944 (1989). Individual unlabeled anti-hVEGF monoclonal antibodies (A4.6.1 or B2.6.2) or irrelevant anti-HGF antibody (IgG1 isotype) were added to the wells of microtiter plates that previously had been coated with hVEGF. Biotinylated anti-hVEGF monoclonal antibodies (BIO-A4.6.1 or BIO-B2.6.2) were then added. The ratio of biotinylated antibody to unlabeled antibody was 1:1000. Binding of the biotinylated antibodies was visualized by the addition of avidin-conjugated peroxidase, followed by o-phenylenediamine dihydrochloride and hydrogen peroxide. The color reaction, indicating the amount of biotinylated antibody bound, was determined by measuring the optical density (O.D) at 495 nm wavelength.

As shown in FIG. 1, in each case, the binding of the biotinylated anti-hVEGF antibody was inhibited by the corresponding unlabeled antibody, but not by the other unlabeled anti-hVEGF antibody or the anti-HGF antibody. These results indicate that the monoclonal antibodies produced by the A4.6.1 and B2.6.2 hybridomas bind to different epitopes within hVEGF.

C. Isotyping

The isotypes of the anti-hVEGF monoclonal antibodies produced by the A4.6.1 and B2.6.2 hybridomas were determined by ELISA. Samples of culture medium (supernatant) in which each of the hybridomas was growing were added to the wells of microtiter plates that had previously been coated with hVEGF. The captured anti-hVEGF monoclonal antibodies were incubated with different isotype-specific alkaline phosphatase-conjugated goat anti-mouse immunoglobulins, and the binding of the conjugated antibodies to the anti-hVEGF monoclonal antibodies was determined by the addition of p-nitrophenyl phosphate. The color reaction was measured at 405 nm with an ELISA plate reader.

By that method, the isotype of the monoclonal antibodies produced by both the A4.6.1 and B2.6.2 hybridomas was determined to be IgG1.

D. Binding Affinity

The affinities of the anti-hVEGF monoclonal antibodies produced by the A4.6.1 and B2.6.2 hybridomas for hVEGF were determined by a competitive binding assays. A predetermined sub-optimal concentration of monoclonal antibody was added to samples containing 20,000-40,000 cpm $^{125}$I-hVEGF (1-2 ng) and various known amounts of unlabeled hVEGF (1-1000 ng). After 1 hour at room temperature, 100 µl of goat anti-mouse Ig antisera (Pel-Freez, Rogers, Ark. USA) were added, and the mixtures were incubated another hour at room temperature. Complexes of antibody and bound protein (immune complexes) were precipitated by the addition of 500 µl of 6% polyethylene glycol (PEG, mol. wt. 8000) at 4° C., followed by centrifugation at 2000×G. for 20 min. at 4° C. The amount of $^{125}$I-hVEGF bound to the anti-hVEGF monoclonal antibody in each sample was determined by counting the pelleted material in a gamma counter.

Affinity constants were calculated from the data by Scatchard analysis. The affinity of the anti-hVEGF monoclonal antibody produced by the A4.6.1 hybridoma was calculated to be $1.2 \times 10^9$ liters/mole. The affinity of the anti-hVEGF monoclonal antibody produced by the B2.6.2 hybridoma was calculated to be $2.5 \times 10^9$ liters/mole.

E. Inhibition of hVEGF Mitogenic Activity

Bovine adrenal cortex capillary endothelial (ACE) cells, Ferrara, et al., Proc. Nat. Acad. Sci. 84:5773 (1987), were seeded at a density of $10^4$ cells/ml in 12 multiwell plates, and 2.5 ng/ml hVEGF was added to each well in the presence or absence of various concentrations of the anti-hVEGF monoclonal antibodies produced by the A4.6.1 or B2.6.2 hybridomas, or an irrelevant anti-HGF monoclonal antibody. After culturing 5 days, the cells in each well were counted in a Coulter counter. As a control, ACE cells were cultured in the absence of added hVEGF.

As shown in FIG. 2, both of the anti-hVEGF monoclonal antibodies inhibited the ability of the added hVEGF to support the growth or survival of the bovine ACE cells. The monoclonal antibody produced by the A4.6.1 hybridoma completely inhibited the mitogenic activity of hVEGF (greater than about 90% inhibition), whereas the monoclonal antibody produced by the B2.6.2 hybridoma only partially inhibited the mitogenic activity of hVEGF.

F. Inhibition of hVEGF Binding

Bovine ACE cells were seeded at a density of $2.5 \times 10^4$ cells/0.5 ml/well in 24 well microtiter plates in Dulbecco's Modified Eagle's Medium (DMEM) containing 10% calf serum, 2 mM glutamine, and 1 ng/ml basic fibroblast growth factor. After culturing overnight, the cells were washed once in binding buffer (equal volumes of DMEM and F12 medium plus 25 mM HEPES and 1% bovine serum albumin) at 4° C.

12,000 cpm $^{125}$I-hVEGF (approx. $5 \times 10^4$ cpm/ng/ml) was preincubated for 30 minutes with 5 µg of the anti-hVEGF monoclonal antibody produced by the A4.6.1, B2.6.2, or A2.6.1 hybridoma (250 µl total volume), and thereafter the mixtures were added to the bovine ACE cells in the microtiter plates. After incubating the cells for 3 hours at 4° C., the cells were washed 3 times with binding buffer at 4° C., solubilized by the addition of 0.5 ml 0.2 N. NaOH, and counted in a gamma counter.

As shown in FIG. 3 (upper), the anti-hVEGF monoclonal antibodies produced by the A4.6.1 and B2.6.2 hybridomas inhibited the binding of hVEGF to the bovine ACE cells. In contrast, the anti-hVEGF monoclonal antibody produced by the A2.6.1 hybridoma had no apparent effect on the binding of hVEGF to the bovine ACE cells. Consistent with the results obtained in the cell proliferation assay described above, the monoclonal antibody produced by the A4.6.1 hybridoma inhibited the binding of hVEGF to a greater extent than the monoclonal antibody produced by the B2.6.2 hybridoma.

As shown in FIG. 3 (lower), the monoclonal antibody produced by the A4.6.1 hybridoma completely inhibited the binding of hVEGF to the bovine ACE cells at a 1:250 molar ratio of hVEGF to antibody.

G. Cross-Reactivity with Other VEGF Isoforms

To determine whether the anti-hVEGF monoclonal antibody produced by the A4.6.1 hybridoma is reactive with the 121- and 189-amino acid forms of hVEGF, the antibody was assayed for its ability to immunoprecipitate those polypeptides.

Human 293 cells were transfected with vectors comprising the nucleotide coding sequence of the 121- and 189-amino acid hVEGF polypeptides, as described. Leung, et al., Science 246:1306 (1989). Two days after transfection, the cells were transferred to medium lacking cysteine and methionine. The cells were incubated 30 minutes in that medium, then 100 µCi/ml of each $^{35}$S-methionine and $^{35}$S-cysteine were added to the medium, and the cells were incubated another two hours. The labeling was chased by transferring the cells to serum free medium and incubating three hours. The cell culture media were collected, and the cells were lysed by incubating for 30 minutes in lysis buffer (150 mM NaCl, 1% NP40, 0.5% deoxycholate, 0.1% sodium dodecyl sulfate (SDS), 50 mM Tris, pH 8.0). Cell debris was removed from the lysates by centrifugation at 200×G. for 30 minutes.

500 µl samples of cell culture media and cell lysates were incubated with 2 µl of A4.6.1 hybridoma antibody (2.4 mg/ml) for 1 hour at 4° C., and then were incubated with 5 µl of rabbit anti-mouse IgG immunoglobulin for 1 hour at 4° C. Immune complexes of $^{35}$S-labeled hVEGF and anti-hVEGF monoclonal antibody were precipitated with protein-A Sepharose (Pharmacia), then subjected to SDS −12% polyacrylamide gel electrophoresis under reducing conditions. The gel was exposed to x-ray film for analysis of the immunoprecipitated, radiolabeled proteins by autoradiography.

The results of that analysis indicated that the anti-hVEGF monoclonal antibody produced by the A4.6.1 hybridoma was cross-reactive with both the 121- and 189-amino acid forms of hVEGF.

Example 3

Preparation of VEGF Receptor—IgG Fusion Proteins

A

The nucleotide and amino acid coding sequences of the flt hVEGF receptor are disclosed in Shibuya, et al., Oncogene 5:519-524 (1990). The coding sequence of the entire extracellular domain of the flt hVEGF receptor was fused to the coding sequence of human IgG1 heavy chain in a two-step process.

Site-directed mutagenesis was used to introduce a BstBI restriction into DNA encoding flt at a site 5' to the codon for amino acid 759 of flt, and to convert the unique BstEII restriction site in plasmid pBSSK⁻FC, Bennett, et al., J. Biol. Chem. 266:23060-23067 (1991), to a BstBI site. The modified plasmid was digested with EcoRI and BstBI and the resulting large fragment of plasmid DNA was ligated together with an EcoRI-BstBI fragment of the flt DNA encoding the extracellular domain (amino acids 1-758) of the flt hVEGF receptor.

The resulting construct was digested with ClaI and NotI to generate an approximately 3.3 kb fragment, which is then inserted into the multiple cloning site of the mammalian expression vector pHEBO2 (Leung, et al., Neuron 8:1045 (1992)) by ligation. The ends of 3.3. kb fragment are modified, for example, by the addition of linkers, to obtain insertion of the fragment into the vector in the correct orientation for expression.

Mammalian host cells (for example, CEN4 cells (Leung, et al. supra) are transfected with the pHEBO2 plasmid containing the flt insert by electroporation. Transfected cells are cultured in medium containing about 10% fetal bovine serum, 2 mM glutamine, and antibiotics, and at about 75% confluency are transferred to serum free medium. Medium is conditioned for 3-4 days prior to collection, and the flt-IgG fusion protein is purified from the conditioned medium by chromatography on a protein-A affinity matrix essentially as described in Bennett, et al., J. Biol. Chem. 266:23060-23067 (1991).
B A human flt-IgG (referred to as hflt(1-3)-IgG) cDNA was constructed as described in Davis-Smyth et al., EMBO J. 15:4919-4927 (1996). This truncated receptor form included only the first three immunoglobulin-like domains of human flt fused to a Fc-IgG. See Ferrara et al., Nature Medicine 4:336 (1998).

A murine flt-IgG (referred to as mflt(1-3)-IgG) was constructed by PCR amplification of mouse 17-day embryo cDNA (Clontech, Palo Alto, Calif.) using primers described in Ferrara et al., supra. The design of the 3' PCR primer ensured that the expression of the mflt-1(1-3) was in frame with a murine IgG2b Fc clone. The resulting 1-kb fragment was first cloned into a TA cloning vector (Invitrogen, San Diego, Calif.) as a ClaI-BstEII fragment. This fragment was ligated to the 5' end of murine IgG2b Fc in a pRK vector. This plasmid enabled the expression of mflt(1-3)-IgG fusion protein when transfected into mammalian cells.

For expression in CHO cells, the cDNAs were subcloned into a dicistronic vector that links the expression of the marker dihydrofolate reductase to the expression of the flt derived fusion protein. See, Lucas et al., Nucleic Acid Res. 24:1774-1779 (1996). Plasmids were introduced into DP12 cells, a derivative of the CHO-K1DUXB11 cell line developed by L. Chasin (Columbia University, New York) via lipofection and selected for growth in glycine-hypoxanthine-thymidine (G-H-T)-free medium. Chisholm et al., DNA Cloning 4:A Practical Approach, Mammalian Systems (eds. Glover & Hames) pp. 1-39 (Oxford Press, 1995). Clones from the first round of selection were subsequently plated at increasing concentrations of methotrexate. Clones were then screened for production by ELISA for the human or murine Fc. Clones that displayed the highest production were adapted to suspension culture, and serum-free cultures were harvested and purified by protein A-Sepharose. Protein concentrations were determined by amino acid analysis. The endotoxin content of the final purified material did not exceed 0.5 eu/mg.

As described in Ferrara et al., supra, both the murine flt(1-3)-IgG fusion protein and the human flt(1-3)-IgG fusion protein were active in inhibiting bioactivity of VEGF in the tested rodent model.

Example 4

Inhibition of Tumor Growth with hVEGF Antagonists

Various human tumor cell lines growing in culture were assayed for production of hVEGF by ELISA. Ovary, lung, colon, gastric, breast, and brain tumor cell lines were found to produce hVEGF. Three cell lines that produced hVEGF, NEG 55 (also referred to as G55) (human glioma cell line obtained from Dr. M. Westphal, Department of Neurosurgery, University Hospital Eppendor, Hamburg, Germany, also referred to as G55), A-673 (human rhabdomyosarcoma cell line obtained from the American Type Culture Collection (ATCC), as cell line number CRL 1598), and SK-LMS-1 (leiomyosarcoma cell line obtained from the ATCC as cell line number HTB 88), were used for further studies.

Six to ten week old female Beige/nude mice (Charles River Laboratory, Wilmington, Mass. USA) were injected subcutaneously with 1-5×10⁶ tumor cells in 100-200 µl PBS. At various times after tumor growth was established, mice were injected intraperitoneally once or twice per week with various doses of A4.6.1 anti-hVEGF monoclonal antibody, an irrelevant anti-gp120 monoclonal antibody (5B6), or PBS. Tumor size was measured every week, and at the conclusion of the study the tumors were excised and weighed.

The effect of various amounts of A4.6.1 anti-hVEGF monoclonal antibody on the growth of NEG 55 tumors in mice is shown in FIGS. 4 and 5. FIG. 4 shows that mice treated with 25 µg or 100 µg of A4.6.1 anti-hVEGF monoclonal antibody beginning one week after inoculation of NEG 55 cells had a substantially reduced rate of tumor growth as compared to mice treated with either irrelevant antibody or PBS. FIG. 5 shows that five weeks after inoculation of the NEG 55 cells, the size of the tumors in mice treated with A4.6.1 anti-hVEGF antibody was about 50% (in the case of mice treated with 25 µg dosages of the antibody) to 85% (in the case of mice treated with 100 µg dosages of the antibody) less than the size of tumors in mice treated with irrelevant antibody or PBS.

The effect of A4.6.1 anti-hVEGF monoclonal antibody treatment on the growth of SK-LMS-1 tumors in mice is shown in FIG. 6. Five weeks after innoculation of the SK-LMS-1 cells, the average size of tumors in mice treated with the A4.6.1 anti-hVEGF antibody was about 75% less than the size of tumors in mice treated with irrelevant antibody or PBS.

The effect of A4.6.1 anti-hVEGF monoclonal antibody treatment on the growth of A673 tumors in mice is shown in FIG. 7. Four weeks after innoculation of the A673 cells, the average size of tumors in mice treated with A4.6.1 anti-hVEGF antibody was about 60% (in the case of mice treated with 10 µg dosages of the antibody) to greater than 90% (in the case of mice treated with 50-400 µg dosages of the antibody) less than the size of tumors in mice treated with irrelevant antibody or PBS.

Example 5

Analysis of the Direct Effect of Anti-hVEGF Antibody on Tumor Cells Growing in Culture NEG55 human glioblastoma cells or A673 rhabdomyosarcoma cells were seeded at a density of $7 \times 10^3$ cells/well in multiwells plates (12 wells/plate) in F12/DMEM medium containing 10% fetal calf serum, 2 mM glutamine, and antibiotics. A4.6.1 anti-hVEGF antibody then was added to the cell cultures to a final concentration of 0-20.0 µg antibody/ml. After five days, the cells growing in the wells were dissociated by exposure to trypsin and counted in a Coulter counter.

FIGS. 8 and 9 show the results of those studies. As is apparent, the A4.6.1 anti-hVEGF antibody did not have any significant effect on the growth of the NEG55 or A673 cells in culture. These results indicate that the A4.6.1 anti-hVEGF antibody is not cytotoxic, and strongly suggest that the observed anti-tumor effects of the antibody are due to its inhibition of VEGF-mediated neovascularization.

Example 6

Effect of Anti-hVEGF Antibody on Endothelial Cell Chemotaxis

Chemotaxis of endothelial cells and others cells, including monocytes and lymphocytes, play an important role in the pathogenesis of rheumatoid arthritis. Endothelial cell migration and proliferation accompany the angiogenesis that occurs in the rheumatoid synovium. Vascularized tissue (pannus) invades and destroys the articular cartilage.

To determine whether hVEGF antagonists interfere with this process, we assayed the effect of the A4.6.1 anti-hVEGF antibody on endothelial cell chemotaxis stimulated by synovial fluid from patients having rheumatoid arthritis. As a control, we also assayed the effect of the A4.6.1 anti-hVEGF antibody on endothelial cell chemotaxis stimulated by synovial fluid from patients having osteoarthritis (the angiogenesis that occurs in rheumatoid arthritis does not occur in osteoarthritis).

Endothelial cell chemotaxis was assayed using modified Boyden chambers according to established procedures. Thompson, et al., Cancer Res. 51:2670 (1991); Phillips, et al., Proc. Exp. Biol. Med. 197:458 (1991). About $10^4$ human umbilical vein endothelial cells were allowed to adhere to gelatin-coated filters (0.8 micron pore size) in 48-well multiwell microchambers in culture medium containing 0.1% fetal bovine serum. After about two hours, the chambers were inverted and test samples (rheumatoid arthritis synovial fluid, osteoarthritis synovial fluid, basic FGF (bFGF) (to a final concentration of 1 µg/ml), or PBS) and A4.6.1 anti-hVEGF antibody (to a final concentration of 10 µg/ml) were added to the wells. After two to four hours, cells that had migrated were stained and counted.

FIG. 10 shows the averaged results of those studies. The values shown in the column labeled "Syn. Fluid" and shown at the bottom of the page for the controls are the average number of endothelial cells that migrated in the presence of synovial fluid, bFGF, or PBS alone. The values in the column labeled "Syn. Fluid+mAB VEGF" are the average number of endothelial cells that migrated in the presence of synovial fluid plus added A4.6.1 anti-hVEGF antibody. The values in the column labeled "% Suppression" indicate the percentage reduction in synovial fluid-induced endothelial cell migration resulting from the addition of anti-hVEGF antibody. As indicated, the anti-hVEGF antibody significantly inhibited the ability of rheumatoid arthritis synovial fluid (53.40 average percentage inhibition), but not osteoarthritis synovial fluid (13.64 average percentage inhibition), to induce endothelial cell migration.

Example 7

Effect of VEGF Antagonist on Cerebral Edema

An in vivo assay was conducted to determine the effects of a flt-IgG antagonist on cerebral edema. Loss of BBB integrity and the formation of cerebral edema often occurs in the pathogenesis of cerebral infarction. It is believed that breakdown of the BBB in ischemic stroke occurs predominantly after the first 24 hours of stroke onset. Further, it is believed that the beneficial effects of prompt and adequate restoration of blood flow following an acute ischemic event may be undermined by reperfusion injury to the cerebral microvasculature comprising the BBB, contributing to the formation of cerebral edema. Klatzo et al. Eds., Brain Edema, Tokyo, Springer (1984), pp. 1-5. The in vivo assay described below was designed to reflect these aspects of the clinical condition.

Focal cortical ischemia was induced in mouse brain by the occlusion of the middle cerebral artery (MCA) using the techniques previously described by Chen et al., Stroke 17:738-743 (1986). The mice (C57BL-6J; 18-25 grams) were anesthetized with 1.5% isoflurane in oxygen. The right MCA was exposed via a craniotomy and ligated with a 11-0 suture. The ipsilateral common carotid artery was also occluded for the ischemic period. The vessels remained occluded for 45 minutes. Prior to surgery, the animals were randomly divided into two groups and either murine flt-IgG (as described in Example 3B above; also described in Ferrara et al., Nature Medicine 4:336 (1998)) or an irrelevant control murine anti-GP120 antibody belonging to the same isotype as the Fc in the flt-IgG [Ferrara et al., supra] was administered intraperitoneally at a dose of 10 mg/kg at 12 hours prior to surgery, at the time of reperfusion and again at 1 and 2 days following surgery. The degree of edema formation was assessed by T2 weighted MR imaging 24 hours following the onset of ischemia. The eventual size of the infarction was assessed 8-12 weeks later using high resolution anatomical MRI. A subset of animals (n=12) were taken for verification of infarction size using conventional histology techniques.

As shown in FIG. 11, administration of flt-Ig caused a significant reduction in the volume of cerebral edema as defined by the region of hyperintensity on the T2-weighted MRI scan acquired 1 day following onset of ischemia (27% reduction, p=0.01 Student's t-test, n=15 and 16 in control and treatment groups, respectively). Representative T2-weighted MR images showing the appearance of cortical edema as a region of high signal intensity compared to the contralateral side is shown in FIG. 12. In this model, progression of ischemic damage leads to loss of cortical tissue and cavitation. The ultimate infarction volume can, therefore, be estimated from high resolution anatomical images by delineating the amount of unaffected cortex and comparing it to the contralateral hemisphere. As shown in FIG. 13, the size of the cortical infarction is significantly reduced by the administration of flt-IgG measured 8-12 weeks later (26% reduction in infarct size, p=0.009 Student's t-test, n=11 and 14 in control and treatment groups, respectively). There was a good correlation between the infarct volume measured by MRI and that determined using conventional histology ($R^2$=0.633). Accordingly, the treated animals exhibited a reduction in development of cerebral edema, which may further provide enhanced neuroprotection. These results indicate that inhibition of the biological activity of VEGF can reduce ischemic-reperfusion related brain edema and injury.

What is claimed is:

1. A method of reducing cerebral edema mediated by VEGF and associated with a non-neoplastic disease, condition, or stimuli in a mammal in need thereof, comprising administering to said mammal an effective amount of an hVEGF antagonist, wherein said hVEGF antagonist interferes with the binding of hVEGF to a cellular receptor, and wherein said hVEGF antagonist comprises an hVEGF receptor fusion protein.

2. The method of claim 1 wherein said disease, condition, or stimuli comprises stroke.

3. The method of claim 2 wherein said mammal has or has had a stroke.

4. The method of claim 3 wherein said hVEGF antagonist is administered as an acute treatment following stroke onset.

5. The method of claim 3 wherein said hVEGF antagonist is administered immediately upon diagnosis or detection of stroke or within approximately 1 to 4 days after onset of the stroke.

6. The method of claim 1 wherein said hVEGF receptor fusion protein comprises an extracellular domain sequence of an hVEGF receptor fused to an immunoglobulin.

7. The method of claim 6 wherein said hVEGF receptor fusion protein comprises a flt-IgG fusion protein.

8. A method of treating ischemic stroke in a mammal in need thereof, comprising administering to said mammal an effective amount of an hVEGF antagonist, wherein the said hVEGF antagonist interferes with the binding of hVEGF to a cellular receptor, and wherein said hVEGF antagonist comprises an hVEGF receptor fusion protein.

9. The method of claim 8 wherein said hVEGF receptor fusion protein comprises an extracellular domain sequence of an hVEGF receptor fused to an immunoglobulin.

10. The method of claim 9 wherein said hVEGF receptor fusion protein comprises a flt-IgG fusion protein.

* * * * *